(12) United States Patent
Lo et al.

(10) Patent No.: US 7,927,788 B2
(45) Date of Patent: *Apr. 19, 2011

(54) BIOMARKERS FOR TOXIC ALGAE

(75) Inventors: Samuel Chun-Lap Lo, Hong Kong SAR (HK); Leo Lai Chan, Hong Kong SAR (HK); Ivor John Hodgkiss, Fleetwood (GB)

(73) Assignee: The Hong Kong Polytechnic University, Hong Kong (CN)

( * ) Notice: Subject to any disclaimer, the term of this patent is extended or adjusted under 35 U.S.C. 154(b) by 301 days.

This patent is subject to a terminal disclaimer.

(21) Appl. No.: 11/812,201

(22) Filed: Jun. 15, 2007

(65) Prior Publication Data

US 2009/0118472 A1 May 7, 2009

Related U.S. Application Data

(62) Division of application No. 10/939,982, filed on Sep. 13, 2004, now Pat. No. 7,109,297.

(51) Int. Cl.
*C12Q 1/00* (2006.01)
*C07H 21/04* (2006.01)
(52) U.S. Cl. .......................... 435/4; 536/23.1
(58) Field of Classification Search .................. None
See application file for complete search history.

(56) References Cited

U.S. PATENT DOCUMENTS

| | | | |
|---|---|---|---|
| 5,223,409 | A | 6/1993 | Ladner et al. |
| 5,283,173 | A | 2/1994 | Fields et al. |
| 5,639,611 | A | 6/1997 | Wallace et al. |
| 5,667,973 | A | 9/1997 | Fields et al. |
| 6,083,698 | A | 7/2000 | Olson et al. |
| 6,638,719 | B1 | 10/2003 | Gunderson et al. |

OTHER PUBLICATIONS

Anderson, et al. 1990. Dynamics and physiology of saxitoxin production by the dinoflagellates *Alexandrium* spp. *Marine Biology*, 104:511-524.
Anderson, et al. 1990. Toxin composition variations in one isolate of the dinoflagellate *Alexandrium fundyense*. *Toxicon*, 28(8):885-893.
Anderson, D. M. Aug. 1994. Red tides. *Scientific American*, pp. 52-58.
Anderson, D. M. 1995. Identification of harmful algal species using molecular probes: An emerging perspective. In P. Lassus, et al. (Eds.), *Harmful Marine Algal Blooms* (pp. 3-13). New York: Lavoisier.
AOAC. 1990. Method 959.08, Paralytic shellfish poison. In *Official Methods of Analyses, Association of Official Analytical Chemists*, 15th Ed. (pp. 881-882). Arlington, VA.
Balech, E. 1995. The genus *Alexandrium* Halim (dinoflagellata), Sherkin Island Marine Station, Sherkin Island. p. 150.
Béchemin, et al. 1999. Effect of different nitrogen/phosphorus nutrient ratios on the toxin content in *Alexandrium minutum*. *Aquatic Microbial Ecology*, 20:157-165.

Boyer, et al. 1987. Effects of nutrient limitation on toxin production and composition in the marine dinoflagellate *Protogonyaulax tamarensis*. *Marine Biology*, 96:123-128.
Bram, et al. 1994. Calcium signalling in T cells stimulated by a cyclophilin B-binding protein. *Nature*, 371:355-358.
Bricelj, et al. 1990. Uptake of *Alexandrium fundyense* by *Mytilus edulis* and *Mercenaria mercenaria* under controlled conditions. In E. Graneli, et al. (Eds.), *Toxic Marine Phytoplankton* (pp. 271-274). New York: Elsevier.
Carrell, et al. 1994. A novel procedure for the synthesis of libraries containing small organic molecules. *Angew. Chem. Int. Ed. Engl.*, 33(20):2059-2061.
Carell, et al. 1994. A solution-phase screening procedure for the isolation of active compounds from a library of molecules. *Angew. Chem. Int. Ed. Engl.*, 33(20):2061-2064.
Catterall, W. A. 1986. Molecular properties of voltage-sensitive sodium channels. *Ann. Rev. Biochem.*, 55:953-985.
Chan, et al. 2004. Use of two-dimensional gel electrophoresis proteome reference maps of dinoflagellates for species recognition of causative agents of harmful algal blooms. *Proteomics*, 4:180-192.
Cho, et al. 1993. An unnatural biopolymer. *Science*, 261:1303-1305.
Cho, et al. 1998. Parallel analysis of genetic selections using whole genome oligonucleotide arrays. *Proc. Natl. Acad. Sci. USA*, 95:3752-3757.
Cook, et al. 2002. DNA microarrays: Implications for cardiovascular medicine. *Circulation Research*, 91:559-564.
Cull, et al. 1992. Screening for receptor ligands using large libraries of peptides linked to the C terminus of the *lac* repressor. *Proc. Natl. Acad. Sci. USA*, 89:1865-1869.
Cwirla, et al. 1990. Peptides on phage. A vast library of peptides for identifying ligands. *Proc. Natl. Acad. Sci. USA*, 87:6378-6382.
Devlin, et al. 1990. Random peptide libraries: A source of specific protein binding molecules. *Science*, 249:404-406.
DeWitt, et al. 1993. "Diversomers": An approach to nonpeptide, nonoligomeric chemical diversity. *Proc. Natl. Acad. Sci. USA*, 90:6909-6913.
Doucette, et al. 1998. Bacterial interactions with harmful algal bloom species: Bloom ecology, toxigenesis, and cytology. In D. M. Anderson, A. D. Cembella & G. M. Hallegraeff (Eds.), *Physiological ecology of harmful algal blooms* (pp. 619-647). Berlin: Springer-Verlag.
Erb, et al. 1994. Recursive deconvolution of combinatorial chemical libraries. *Proc. Nati. Acad. Sci. USA*, 91:11422-11426.
Felici, et al. 1991. Selection of antibody ligands from a large library of oligopeptides expressed on a multivalent exposition vector. *J. Mol. Biol.*, 222:301-310.
Fields, et al. 1989. A novel genetic system to detect protein-protein interactions. *Nature*, 340:245-246.
Flynn, et al. 1996. Comparisons among species of *Alexandrium* (Dinophyceae) grown in nitrogen- or phosphorus-limiting batch culture. *Marine Biology*, 126:9-18.

(Continued)

*Primary Examiner* — Suzanne M. Noakes
(74) *Attorney, Agent, or Firm* — George G. Wang; Wilkinson & Grist

(57) ABSTRACT

The present invention is directed toward biomarkers that identify characteristics of algae. The invention is further directed toward biomarkers that serve to identify algae species and strains of algae species as well as detect the presence of algal toxins. Additional embodiments feature methods utilizing algal biomarkers and polypeptides that can serve as biomarkers.

4 Claims, 28 Drawing Sheets

OTHER PUBLICATIONS

Fodor, et al. 1993. Multiplexed biochemical assays with biological chips. *Nature*, 364:555-556.

Franco, et al. 1994. Toxin profiles of natural populations and cultures of *Alexandrium minutum* Halim from Galician (Spain) coastal waters. *Journal of Applied Phycology*, 6:275-279.

Frohman, et al. 1988. Rapid production of full-length cDNAs from rare transcripts: Amplification using a single gene-specific oligonucleotide primer. *Proc. Natl. Acad. Sci. USA*, 85:8998-9002.

Fromont-Racine, et al. 1997. Toward a functional analysis of the yeast genome through exhaustive two-hybrid screens. *Nature Genetics*, 16:277-282.

Gallop, et al. 1994. Applications of combinatorial technologies to drug discovery. 1. Background and peptide combinatorial libraries. *Journal of Medicinal Chemistry*, 37(9):1233-1251.

Harper, et al. 1993. The p21 Cdk-interacting protein Cip1 is a potent inhibitor of G1 cyclin-dependent kinases. *Cell*, 75:805-816.

Houghten, et al. 1992. The use of synthetic peptide combinatorial libraries for the identification of bioactive peptides. *BioTechniques*, 13(3):412-421.

Jellett, et al. 1992. Paralytic shellfish poison (saxitoxin family) bioassays: Automated endpoint determination and standardization of the in vitro tissue culture bioassay, and comparison with the standard mouse bioassay. *Toxicon*, 30(10):1143-1156.

Keller, et al. 1987. Media for the culture of oceanic ultraphytoplankton. *J. Phycol.*, 23:633-638.

Lam, et al. 1991. A new type of synthetic peptide library for identifying ligand-binding activity. *Nature*, 354:82-84.

Lam, K. S. 1997. Application of combinatorial library methods in cancer research and drug discovery. *Anti-Cancer Drug Design*, 12:145-167.

Lawrence, et al. 2004. Quantitative determination of paralytic shellfish poisoning toxins in shellfish using prechromatographic oxidation and liquid chromatography with fluorescence detection: Interlaboratory study. *Journal of AOAC International*, 87(1):83-100.

Lichter, et al. 2000. Comparative genomic hybridization. Uses and limitations. *Seminars in Hematology*, 37(4):348-357.

Loeblich, A. R. III. 1984. Dinoflagellate physiology and biochemistry. In D. L. Spector (Ed.), *Dinolagellates* (pp. 299-342). Orlando: Academic Press.

MacBeath, et al. 2000. Printing proteins as microarrays for high-throughput function determination. *Science*, 289:1760-1763.

Maranda, et al. 1985. Comparison of toxicity between populations of *Gonyaulax tamarensis* of eastern North American waters. *Estuarine, Coastal Shelf Science*, 21:401-410.

McConnell, et al. 1992. The cytosensor microphysiometer: Biological applications of silicon technology. *Science*, 257:1906-1912.

Ogata, et al. 1989. Effect of water temperature and light intensity on growth rate and toxin production of toxic dinoflagellates. In T. Okaichi, et al. (Eds.), *Red Tides: Biology Environmental Science and Toxicology* (pp. 423-426). New York: Elsevier.

Ohara, et al. 1989. One-sided polymerase chain reaction: The amplification of cDNA. *Proc. Natl. Acad. Sci. USA*, 86:5673-5677.

Oshima, et al. 1989. Production of paralytic shellfish toxins by the dinoflagellate *Alexandrium minutum* Halim from Australia. *Nippon Suisan Gakkaishi*, 55(5):925.

Oshima, et al. 1993. Comparative study on paralytic shellfish toxin profiles of the dinoflagellate *Gymnodinium catenatum* from three different countries. *Marine Biology*, 116:471-476.

Oshima, Y. 1995. Postcolumn derivatization liquid chromatographic method for paralytic shellfish toxins. *Journal of AOAC International*, 78(2):528-532.

Palenik, et al. 1998. Molecular markers of phytoplankton physiological status and their application at the level of individual cells. In K. E. Cooksey (Ed.), *Molecular Approaches to the Study of the Ocean* (pp. 187-205). London: Chapman and Hall.

Quilliam, et al. 1993. Characterization of the oxidation products of paralytic shellfish poisoning toxins by liquid chromatography/mass spectrometry. *Rapid Communications in Mass Spectrometry*, 7:482-487.

Scott, et al. 1990. Searching for peptide ligands with an epitope library. *Science*, 249:386-390.

Shevchenko, et al. 1996. Mass spectrometric sequencing of proteins from silver-stained polyacrylamide gels. *Analytical Chemistry*, 68:850-858.

Shimizu, Y., 1993. Microalgal metabolites. *Chem. Rev.*, 93:1685-1698.

Sullivan, J. J. 1990. High-performance liquid chromatographic method applied to paralytic shellfish poisoning research. In S. Hall & G. Strichartz (Eds.), *Marine Toxins: Origin, Structure, and Molecular Pharmacology* (pp. 66-77). Washington: American Chemical Society.

Taroncher-Oldenburg, et al. 1997. Toxin variability during the cell cycle of the dinoflagellate *Alexandrium fundyense*. *Limnol. Oceanogr.*, 42:1178-1188.

Taylor, F. J. R. 1993. The species problem and its impact on harmful phytoplankton studies. In T. J. Smayda & Y. Shimizu (Eds.), *Toxic Phytoplankton Blooms in the Sea* (pp. 81-86). New York: Elsevier.

Tusher, et al. 2001. Significance analysis of microarrays applied to the ionizing radiation response. *Proc. Natl. Acad. Sci. USA*, 98(9):5116-5121.

Vrieling, et al. 1996. Immunofluorescence in phytoplankton research: Applications and potential. *J. Phycol.*, 32:1-16.

Wang, et al. 2001. Dynamics of C2 toxin and chlorophyll-$\alpha$ formation in the dinoflagellate *Alexandrium tamarense* during large scale cultivation. *Toxicon*, 39:1533-1536.

Wang, et al. 2003. Effect of antibiotic treatment on toxin production by *Alexandrium tamarense*. *Biomedical and Environmental Sciences*, 16(4):340-347.

Wilkins, et al. 1997. Cross-species protein identification using amino acid composition, peptide mass fingerprinting, isoelectric point and molecular mass: A theoretical evaluation. *J. Theor. Biol.*, 186:7-15.

Yentsch, et al. 1978. Coexistence of toxic and nontoxic dinoflagellates resembling *Gonyaulax tamarensis* in New England coastal waters (NW Atlantic). *J. Phycol.* 14:330-332.

Zuckermann, et al. 1994. Discovery of nanomolar ligands for 7-transmembrane G-protein-coupled receptors from a diverse *N*-(substituted)glycine peptoid library. *J. Med. Chem.*, 37:2678-2685.

GenBank Accession No. CF751900 (Deposited Oct. 10, 2003).

Chan, et al., "Identification and characterization of a "biomarker of toxicity" from the proteome of the paralytic shellfish toxin-producing dinoflagellate *Alexandrium tamarense* (Dinophyceae)", Proteomics, 6, 654-666, 2006.

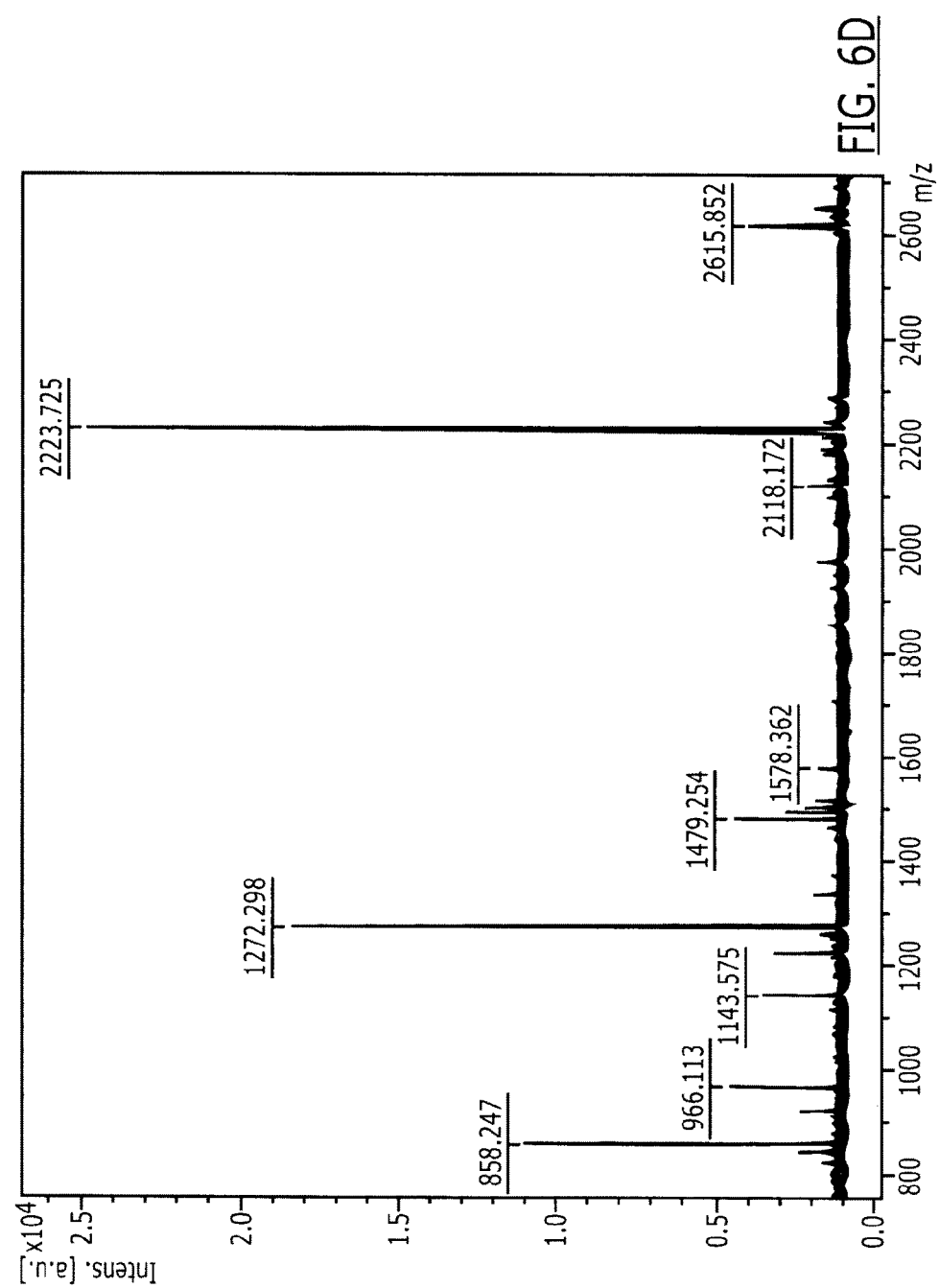

BIOMARKERS FOR TOXIC ALGAE

RELATED APPLICATION

This application is a divisional of allowed U.S. patent application Ser. No. 10/939,982, filed Sep. 13, 2004 now U.S. Pat. No. 7,109,297, the entire contents of which are incorporated herein by reference.

BACKGROUND OF THE INVENTION

1. Field of the Invention

The present invention relates to biochemical methods of detecting and/or classifying the species and/or strain of an alga and detecting the presence of toxins of algal origin.

2. Description of the Related Art

Contamination of shellfish with toxins produced by aquatic organisms is an on-going problem with the shellfish industry and aquaculture worldwide. Bans on the sale and consumption of shellfish from discrete coastline regions are often provoked by toxic harmful algal blooms (HABs). HABs are harmful to both human consumers and the ecosystem as a whole, as toxins produced by algae can sicken and kill many forms of aquatic organisms. Further, contamination of shellfish with algal toxins can occur in the absence of observed HABs. Hence the need for continuous surveillance programs to protect the public from food-borne illness due to contaminated shellfish.

Consumption of shellfish contaminated with algal toxin can lead to paralytic shellfish poisoning (PSP), a serious and potentially fatal illness. There are several types of PSP toxins (PST): saxitoxin (STX), neosaxitoxin (NFO), gonyautoxins 2 and 3 (GTX2,3), gonyautoxins 1 and 4 (GTX1,4), decarbamoyl saxitoxin (dcSTX), B-1 (GTX5), C-1 and C-2 (C1,2), C-3 and C-4 (C3,4) and B-2 (GTX6) toxin [1]. STX, one of the more common ones, causes paralytic symptoms in an organism by acting as a potent sodium channel blocker [2]. PST are poisonous to organisms higher up the food chain [3] due to the accumulation in bivalves of a range of neurotoxins produced by several dinoflagellates, particularly those of the genera *Alexandrium*, *Gymnodinium* and *Pyrodinium*.

Rapid and reliable species identification is a requirement for both scientific research into HABs and commercial monitoring programs for the shellfish industry. In general algae research, morphological criteria are sufficient to classify unicellular algae to species, and to identify potentially toxin-producing dinoflagellates. Difficulties arise, however, if morphological characteristics that distinguish one alga from the rest of the plankton community are lacking. For instance, some morphospecies have proven to be consistently linked to toxicity [e.g., A. catenella (Whedon et Kofoid) has been found to be constantly toxic], but other morphospecies such as A. tamarense (Lebour) and Balech Talyor are known to exist in both toxic and non-toxic strains [4]. Even with considerable time and effort, morphospecies (which exist in both toxic and non-toxic strains) might not be able to be differentiated by traditional microscopy since they may have identical morphology. To remedy these problems, identification methods that use molecular probes for nucleic acids or species-specific antibodies to detect specific toxin-producing algae strains have been developed [5,6]. However these approaches suffer from cross-reactivity between species and strains, as well as the diversity of algae species, strains and their toxins.

The study and identification of PSTs in the laboratory has been performed using a variety of biological, biochemical and chemical analytical procedures. Among them, biochemical (ELISA, receptor binding), tissue culture bioassays [7], mouse bioassays [8] or sophisticated chemical analytical alternatives (HPLC-FD [9] and LC-MS [10], etc) for routine toxin monitoring. They are configured to yield extremely high sensitivity and specificity towards the target toxin analyte. However, limited availability of pure toxins commercially and the large variation in specificity of the antibody to individual toxins hampered their application.

There exists a need for new methods of identifying species and strains of algae and detecting the presence or absence of algal toxins.

SUMMARY OF THE INVENTION

The present invention relates to biomarkers useful for determining characteristics of algae and for detecting algal toxins. Thus, embodiments of the present invention include methods of using, detecting and manipulating algal biomarkers as well as the biomarkers themselves.

One aspect of the present invention relates to a method of identifying the toxicity of a strain of algae, comprising obtaining a profile of a plurality of proteins expressed by algae in a sample of algae of unknown toxicity, obtaining protein profiles of non-toxic and toxic strains of algae, comparing said protein profile from said sample of algae of unknown toxicity to said protein profiles of non-toxic and toxic strains of algae and identifying said toxicity of a strain of algae based on said comparing of the protein profiles. Additional embodiments comprise an assay for said profile of a plurality of proteins selected from the group consisting of 2-DE gel electrophoresis, ELISA, HPLC, peptide mass fingerprinting, matrix-assisted laser desorption ionization-time of flight mass spectrometry (MALDI-TOF MS), protein arrays and nucleic acid arrays. In some embodiments, fluorescence detection is used with said HPLC. Additional embodiments comprise an assay for said profile of a plurality of proteins, wherein said assay uses a technology selected from the group consisting of Southern blotting, nucleotide sequencing, polymerase chain reaction, mass spectroscopy and nucleic acid array hybridization.

Additional aspects of the invention include methods for determining whether an alga is a toxic strain of the algae species *Alexandrium*, comprising evaluating the levels of expression of a compound selected from the group consisting of a polypeptide comprising the sequence (SEQ ID NO: 1,
SAEYLERLGPKDADVPFTAAPGGAEHPVTFKKRPFGILRYQPGAGMKGAM

VMEIIPKSRYPGDPQGQAFSSGVQSGWVVKSINGEDVLTADFGRIMDLLD

DEVADPRFSKSTALALEKQGGRLAAPVEAPLGVVFAEIPGYQGNFATLSQ

DGQDGFAR, hereafter called T1) and a nucleic acid comprising a sequence encoding a polypeptide comprising the amino acid sequence of T1 (e.g.

(SEQ ID NO: 2))
AGTGCCGAGTACCTAGAACGACTAGGGCCCAAAGACGCGGACGTGCCCTT

CACGGCCGCCCCTGGCGGCGCTGAGCACCCGGTGACCTTCAAGAAGCGGC

CCTTCGGCATCTTGCGCTACCAGCCGGGCGCGGGCATGAAGGGTGCCATG

GTGATGGAGATCATTCCCAAGTCGCGCTACCCCGGCGACCCCCAGGGCCA

GGCGTTCTCCTCGGGCGTGCAGAGCGGATGGGTCGTCAAGTCGATCAACG

-continued

```
GTGAGGACGTGCTGACGGCGGACTTCGGCCGCATCATGGACTTGCTGGAC

GACGAGGTGGCCGACCCGCGCTTCTCCAAGTCGACGGCCTTGGCCCTCGA

GAAGCAGGGCGGCCGCTTGGCAGCGCCGGTGGAGGCGCCCCTCGGGGTCG

TCTTCGCGGAGATCCCGGGCTACCAGGGCAACTTCGCGACGCTCAGCCAG

GACGGCCAGGACGGCTTCGCGCGTTA.
```

Additional embodiments of the invention include kits for carrying out the methods of the invention. In some embodiments, kits are designed to carry out steps in a method of identifying the toxicity of a strain of algae, comprising steps to analyze the proteinaceous contents of a sample of algae. Additional embodiments feature kits designed to carry out steps in a method for determining whether an alga is a toxic strain of an algae species, comprising a nucleic acid selected from the group consisting of a nucleic acid comprising a sequence encoding a polypeptide comprising the amino acid sequence of T1 and a nucleic acid comprising a sequence that is complementary to a sequence encoding a polypeptide comprising the amino acid sequence of T1.

In some embodiments of these methods, said alga is a strain selected from the group consisting of AMKS2, AMKS3, AMKS4, AMTK4, AMTK7, AMTK3, AMTK5 and AMTK6. Some embodiments comprise an assay for said polypeptide comprising the sequence T1, wherein the assay is selected from the group consisting of 2-DE gel electrophoresis, ELISA, HPLC, peptide mass fingerprinting, MALDI-TOF mass spectrometry, 3' rapid amplification of cDNA ends (3' RACE) cloning, protein arrays and nucleic acid arrays. Fluorescence detection is used with said HPLC in some embodiments. Additional embodiments comprise an assay for said nucleic acid comprising a sequence encoding a polypeptide comprising the sequence T1, wherein said assay uses a technology selected from the group consisting of Southern blotting, nucleotide sequencing, 3' RACE cloning, polymerase chain reaction, MALDI-TOF mass spectrometry and nucleic acid array hybridization.

Embodiments of the invention also include an isolated polypeptide comprising the sequence T1. In some embodiments, said polypeptide is of algal origin. The presence of said polypeptide is indicative of a characteristic of the alga of origin in additional embodiments. Still more embodiments feature said characteristic as being selected from the group consisting of the species to which the alga belongs, the strain to which the alga belongs and the presence of toxin.

Additional embodiments include an isolated nucleic acid comprising a sequence encoding a polypeptide comprising the sequence T1. In additional embodiments, said nucleic acid is obtained from algae of the genus *Alexandrium*.

Further embodiments relate to an isolated nucleic acid comprising the full-length coding sequence of the T1 protein obtained through a process comprising designing complimentary degenerate oligonucleotide primers based on a sequence encoding a polypeptide comprising the sequence T1, performing reverse transcription PCR on an algae RNA sample by reverse transcription PCR using said complimentary degenerate primers and isolating the full-length coding sequence of the T1 protein from other RT-PCR products. Some embodiments feature said isolated nucleic acid wherein said isolating of said full-length coding sequence comprises screening genetic expression libraries comprising genetic sequence from algae.

Additional embodiments include a method of screening for and identifying a compound that binds to a polypeptide comprising the sequence T1, comprising: contacting said polypeptide with said compound and determining whether said compound binds to said polypeptide. Some embodiments comprise said method wherein said compound is a polypeptide. Other embodiments comprise said method wherein said compound is not a polypeptide.

In further embodiments of the invention, a nucleotide array is featured, comprising a nucleotide sequence comprising a sequence encoding a polypeptide comprising the sequence T1. Additional embodiments include a protein array comprising a polypeptide comprising the sequence T1.

One aspect of the present invention comprises a method of determining a characteristic of an alga, comprising obtaining a sample of biological material comprising biological material from said alga, and performing an non-morphological assay to determine the presence or absence of a biomarker for said characteristic of said alga in said sample of biological material. In an additional embodiment of the invention, the method determines a characteristic selected from the group consisting of the species to which the alga belongs, the strain to which the alga belongs and the presence of toxin. In some embodiments of the invention, the species of algae for which characteristics are being determined is *Alexandrium minutum*. Additional embodiments include methods where the algae belong to a strain of *A. minutum* selected from the group consisting of AMKS2, AMKS3, AMKS4, AMTK4, AMTK7, AMTK3, AMTK5 and AMTK6. In some embodiments, the toxin whose presence is being determined is a cyclic perhydropurine saxitoxin. In further embodiments, the cyclic perhydropurine saxitoxin is selected from the group consisting of gonyautoxin 1, gonyautoxin 2, gonyautoxin 3 and gonyautoxin 4.

Additional embodiments of the invention are methods of determining a characteristic of an alga, comprising obtaining a sample of biological material comprising material from said alga, and performing an assay to determine the presence or absence of a biomarker for said characteristic of said alga in said sample of biological material, wherein said biological material comprises material selected from the group consisting of whole algae, an extract or lysate of algae and a sample of tissue from an aquatic organism. Further embodiments feature methods wherein said aquatic organism is selected from the group consisting of a bivalve, an invertebrate, a fish and a mammal. Additional embodiments include methods where said material from an alga is selected from the group consisting of proteinaceous material from algae and nucleic acid from algae. Some embodiments feature methods wherein said assay determines the presence of a molecule selected from the group consisting of an algal protein and an algal nucleic acid. In particular embodiments of the invention, said assay for determining the presence of an algal protein uses a technology selected from the group consisting of 2-DE gel electrophoresis, ELISA, HPLC, peptide mass fingerprinting, 3' RACE cloning, a protein array, a nucleic acid array and MALDI-TOF mass spectrometry. Further embodiments include methods wherein fluorescence detection is used with said HPLC. Some embodiments comprise methods wherein said assay for determining the presence of an algal nucleic acid uses a technology selected from the group consisting of Southern blotting, nucleotide sequencing, polymerase chain reaction, 3' RACE cloning, MALDI-TOF mass spectrometry and array hybridization.

Additional embodiments comprise methods wherein said biomarker comprises a molecule selected from the group consisting of a peptide comprising the sequence of a non-saxitoxin algal protein and a nucleotide comprising genetic sequence from a gene encoding a non-saxitoxin algal protein.

Said non-saxitoxin algal protein comprises the peptide sequence SAEYL ERLGP KDADV PFTAA AGGGE EPVVF DDRP (SEQ ID NO: 3) in some methods of further embodiments. In some methods of further embodiments, the non-saxitoxin algal protein comprises the sequence SAEYL ERLGP KDADV PFTAA PGGPE HPVTF DKRP (SEQ ID NO: 4). In other embodiments the non-saxitoxin algal protein comprises the sequence SAEYL ERLGP KDADV PFTAA PGGPE HSVTF FKRP (SEQ ID NO: 5).

Additional embodiments of the invention comprise a polypeptide comprising the N-terminal amino acid sequence of

```
                                              (SEQ ID NO: 1)
SAEYLERLGPKDALDVPFTAAPGGAEHPVTFKKRPFGILRYQPGAGMKGA

MVMEIIPKSRYPGDPQGQAFSSGVQSGWVVKSIINGEDVLTADFGRIMDL

LDDEVADPRFSKSTALALEKQGGRLAAPVEAPLGVVFAEIPGYQGNFATL

SQDGQDGFAR.
```

Some embodiments feature said N-terminal amino acid sequence wherein said polypeptide is of algal origin. Further embodiments include polypeptides wherein the presence of said polypeptide is indicative of a characteristic of the alga of origin. Additional embodiments comprise polypeptides wherein said characteristic indicative of the alga of origin is selected from the group consisting of the species to which the alga belongs, the strain to which the alga belongs and the presence of toxin.

One embodiment of the present invention is an isolated polypeptide comprising SEQ ID NO: 1. In some aspects of this embodiment, the polypeptide is of algal origin. In other aspects of this embodiment, the presence of said polypeptide is indicative of a characteristic of the alga of origin. For example, in some embodiments, the characteristic may be selected from the group consisting of the species to which the alga belongs, the strain to which the alga belongs and the presence of toxin.

Another embodiment of the present invention is an isolated polypeptide selected from the group consisting of a polypeptide comprising at least 10 consecutive amino acids of SEQ ID NO: 1, a polypeptide comprising at least 20 consecutive amino acids of SEQ ID NO: 1, a polypeptide comprising at least 30 consecutive amino acids of SEQ ID NO: 1, and a polypeptide comprising more than 30 consecutive amino acids of SEQ ID NO: 1. In some aspects of this embodiment, the polypeptide comprises a sequence selected from the group consisting of AP, PG, GA, AE, EH, HP, PV, VT, TF, FK, KK and KR.

Another embodiment of the present invention is an isolated nucleic acid encoding the polypeptide of SEQ ID NO: 1. In some aspects of this embodiment, the nucleic acid comprises SEQ ID NO: 2.

Another embodiment of the present invention is an isolated nucleic acid selected from the group consisting of a nucleic acid comprising at least 10 consecutive nucleotides of SEQ ID NO: 2, a nucleic acid comprising at least 20 consecutive nucleotides of SEQ ID NO: 2, a nucleic acid comprising at least 30 consecutive nucleotides of SEQ ID NO: 2, a nucleic acid comprising at least 40 consecutive nucleotides of SEQ ID NO: 2, a nucleic acid comprising at least 50 consecutive nucleotides of SEQ ID NO: 2, and a nucleic acid comprising more than 50 consecutive nucleotides of SEQ ID NO: 2.

Another embodiment of the present invention is a method for determining whether a strain of algae is toxic comprising determining whether a sample obtained from said strain of algae comprises a polypeptide of SEQ ID NO: 1 or a portion thereof or a nucleic acid encoding a polypeptide of SEQ ID NO: 1 or a portion thereof. In some aspects of the method, the portion of SEQ ID NO: 1 comprises a portion of SEQ ID NO: 1 selected from the group consisting of:

(a) a portion of SEQ ID NO: 1 which includes the sequence AP;

(b) a portion of SEQ ID NO: 1 which includes the sequence PG;

(c) a portion of SEQ ID NO: 1 which includes the sequence GA;

(d) a portion of SEQ ID NO: 1 which includes the sequence AE;

(e) a portion of SEQ ID NO: 1 which includes the sequence EH;

(f) a portion of SEQ ID NO: 1 which comprises the sequence HP;

(g) a portion of SEQ ID NO: 1 which includes the sequence PV;

(h) a portion of SEQ ID NO: 1 which includes the sequence VT;

(i) a portion of SEQ ID NO: 1 which includes the sequence TF;

(j) a portion of SEQ ID NO: 1 which includes the sequence FK;

(k) a portion of SEQ ID NO: 1 which includes the sequence KK; and (l) a portion of SEQ ID NO: 1 which includes the sequence KR.

Another embodiment of the present invention is a method for determining whether a strain of algae is toxic comprising determining whether a sample obtained from said strain of algae comprises a polypeptide of SEQ ID NO: 3 or a portion thereof or a nucleic acid encoding a polypeptide of SEQ ID NO: 3 or a portion thereof. In some aspects of the method, the portion of SEQ ID NO: 3 comprises a portion of SEQ ID NO: 3 selected from the group consisting of:

(a) a portion of SEQ ID NO: 3 which includes the sequence AAA;

(b) a portion of SEQ ID NO: 3 which includes the sequence AG;

(c) a portion of SEQ ID NO: 3 which includes the sequence GGG;

(d) a portion of SEQ ID NO: 3 which includes the sequence GE;

(e) a portion of SEQ ID NO: 3 which includes the sequence EE;

(f) a portion of SEQ ID NO: 3 which includes the sequence EP;

(g) a portion of SEQ ID NO: 3 which includes the sequence VV;

(h) a portion of SEQ ID NO: 3 which includes the sequence VF;

(i) a portion of SEQ ID NO: 3 which includes the sequence FD; and (j) a portion of SEQ ID NO: 3 which includes the sequence DD Another embodiment of the present invention is a method for determining whether a strain of algae is toxic comprising determining whether a sample obtained from said strain of algae comprises a polypeptide of SEQ ID NO: 4 or a portion thereof or a nucleic acid encoding a polypeptide of SEQ ID NO: 4 or a portion thereof. In some aspects of the method, the portion of SEQ ID NO: 4 is selected from the group consisting of:

(a) comprises a portion of SEQ ID NO: 4 which includes the sequence GGP;
(b) a portion of SEQ ID NO: 3 which includes the sequence PE;
(c) a portion of SEQ ID NO: 3 which includes the sequence FD; and
(d) a portion of SEQ ID NO: 3 which includes the sequence DK.

Another embodiment of the present invention is a method for determining whether a strain of algae is toxic comprising determining whether a sample obtained from said strain of algae comprises a polypeptide of SEQ ID NO: 5 or a portion thereof or a portion thereof or a nucleic acid encoding a polypeptide of SEQ ID NO: 5 or a portion thereof. In some aspects of the method, the portion of SEQ ID NO: 5 comprises a portion of SEQ ID NO: 5 selected from the group consisting of:
(a) portion of SEQ ID NO: 5 which includes the sequence GGP;
(b) a portion of SEQ ID NO: 5 which includes the sequence PE;
(c) a portion of SEQ ID NO: 5 which includes the sequence HS;
(d) a portion of SEQ ID NO: 5 which includes the sequence SV;
(e) a portion of SEQ ID NO: 5 which includes the sequence FF.

Another embodiment of the present invention is a kit comprising reagents for determining whether a strain of algae comprises a polypeptide selected from the group consisting of the polypeptide of SEQ ID NO: 1, the polypeptide of SEQ ID NO: 3, the polypeptide of SEQ ID NO: 4, the polypeptide of SEQ ID NO: 5 or a portion of any of the foregoing polypeptides. In some aspects, the kit comprises an antibody which can distinguish the toxicity associated polypeptide comprising SEQ ID NO: 1 from a polypeptide which is not associated with toxicity. In some aspects of the kit, the polypeptide which is not associated with toxicity is a polypeptide comprising a sequence selected from the group consisting of SEQ ID NO: 3, SEQ ID NO: 4, and SEQ ID NO: 5. In some aspects of the kit the antibody is capable of determining whether said strain of algae comprises a polypeptide selected from the group consisting of:
(1) a portion of SEQ ID NO: 1 which includes the sequence AP;
(2) a portion of SEQ ID NO: 1 which includes the sequence PG;
(3) a portion of SEQ ID NO: 1 which includes the sequence GA;
(4) a portion of SEQ ID NO: 1 which includes the sequence AE;
(5) a portion of SEQ ID NO: 1 which includes the sequence EH;
(6) a portion of SEQ ID NO: 1 which comprises the sequence HP;
(7) a portion of SEQ ID NO: 1 which includes the sequence PV;
(8) a portion of SEQ ID NO: 1 which includes the sequence VT;
(9) a portion of SEQ ID NO: 1 which includes the sequence TF;
(10) a portion of SEQ ID NO: 1 which includes the sequence FK;
(11) a portion of SEQ ID NO: 1 which includes the sequence KK;
(12) a portion of SEQ ID NO: 1 which includes the sequence KR;
(13) a portion of SEQ ID NO: 3 which includes the sequence AAA;
(14) a portion of SEQ ID NO: 3 which includes the sequence AG;
(15) a portion of SEQ ID NO: 3 which includes the sequence GGG;
(16) a portion of SEQ ID NO: 3 which includes the sequence GE;
(17) a portion of SEQ ID NO:3 which includes the sequence EE;
(18) a portion of SEQ ID NO: 3 which includes the sequence EP;
(19) a portion of SEQ ID NO: 3 which includes the sequence VV;
(20) a portion of SEQ ID NO: 3 which includes the sequence VF;
(21) a portion of SEQ ID NO: 3 which includes the sequence FD;
(22) a portion of SEQ ID NO: 3 which includes the sequence DD;
(23) a portion of SEQ ID NO: 4 which includes the sequence GGP;
(24) a portion of SEQ ID NO: 3 which includes the sequence PE;
(25) a portion of SEQ ID NO: 3 which includes the sequence FD;
(26) a portion of SEQ ID NO: 3 which includes the sequence DK;
(27) a portion of SEQ ID NO: 5 which includes the sequence GGP;
(28) a portion of SEQ ID NO: 5 which includes the sequence PE;
(29) a portion of SEQ ID NO: 5 which includes the sequence HS;
(30) a portion of SEQ ID NO: 5 which includes the sequence SV; and
(31) a portion of SEQ ID NO: 5 which includes the sequence FF.

In some aspects of the kit, the kit comprises a nucleic acid probe or primer which can distinguish a nucleic acid encoding the toxicity associated polypeptide comprising SEQ ID NO: 1 from a nucleic acid which encodes a polypeptide which is not associated with toxicity. In some aspects of the kit, the nucleic acid encoding the toxicity associated polypeptide of SEQ ID NO: 1 comprises SEQ ID NO: 2. In some aspects of the kit, the nucleic acid probe or primer can distinguish a nucleic acid encoding the toxicity associated polypeptide comprising SEQ ID NO: 1 from a nucleic acid encoding a polypeptide selected from the group consisting of SEQ ID NO: 3, SEQ ID NO: 4 and SEQ ID NO: 5. In some aspects of the kit, the nucleic acid probe or primer is capable of determining whether said strain of algae comprises a nucleic acid encoding a polypeptide selected from the group consisting of:
(1) a portion of SEQ ID NO: 1 which includes the sequence AP;
(2) a portion of SEQ ID NO: 1 which includes the sequence PG;
(3) a portion of SEQ ID NO: 1 which includes the sequence GA;
(4) a portion of SEQ ID NO: 1 which includes the sequence AE;
(5) a portion of SEQ ID NO: 1 which includes the sequence EH;
(6) a portion of SEQ ID NO: 1 which comprises the sequence HP;
(7) a portion of SEQ ID NO: 1 which includes the sequence PV;

(8) a portion of SEQ ID NO: 1 which includes the sequence VT;

(9) a portion of SEQ ID NO: 1 which includes the sequence TF;

(10) a portion of SEQ ID NO: 1 which includes the sequence FK;

(11) a portion of SEQ ID NO: 1 which includes the sequence KK;

(12) a portion of SEQ ID NO: 1 which includes the sequence KR;

(13) a portion of SEQ ID NO: 3 which includes the sequence AAA;

(14) a portion of SEQ ID NO: 3 which includes the sequence AG;

(15) a portion of SEQ ID NO: 3 which includes the sequence GGG;

(16) a portion of SEQ ID NO: 3 which includes the sequence GE;

(17) a portion of SEQ ID NO: 3 which includes the sequence EE;

(18) a portion of SEQ ID NO: 3 which includes the sequence EP;

(19) a portion of SEQ ID NO: 3 which includes the sequence VV;

(20) a portion of SEQ ID NO: 3 which includes the sequence VF;

(21) a portion of SEQ ID NO: 3 which includes the sequence FD;

(22) a portion of SEQ ID NO: 3 which includes the sequence DD;

(23) a portion of SEQ ID NO: 4 which includes the sequence GGP;

(24) a portion of SEQ ID NO: 3 which includes the sequence PE;

(25) a portion of SEQ ID NO: 3 which includes the sequence FD;

(26) a portion of SEQ ID NO: 3 which includes the sequence DK;

(27) a portion of SEQ ID NO: 5 which includes the sequence GOP;

(28) a portion of SEQ ID NO: 5 which includes the sequence PE;

(29) a portion of SEQ ID NO: 5 which includes the sequence HS;

(30) a portion of SEQ ID NO: 5 which includes the sequence SV; and

(31) a portion of SEQ ID NO: 5 which includes the sequence FF.

Figure 1:
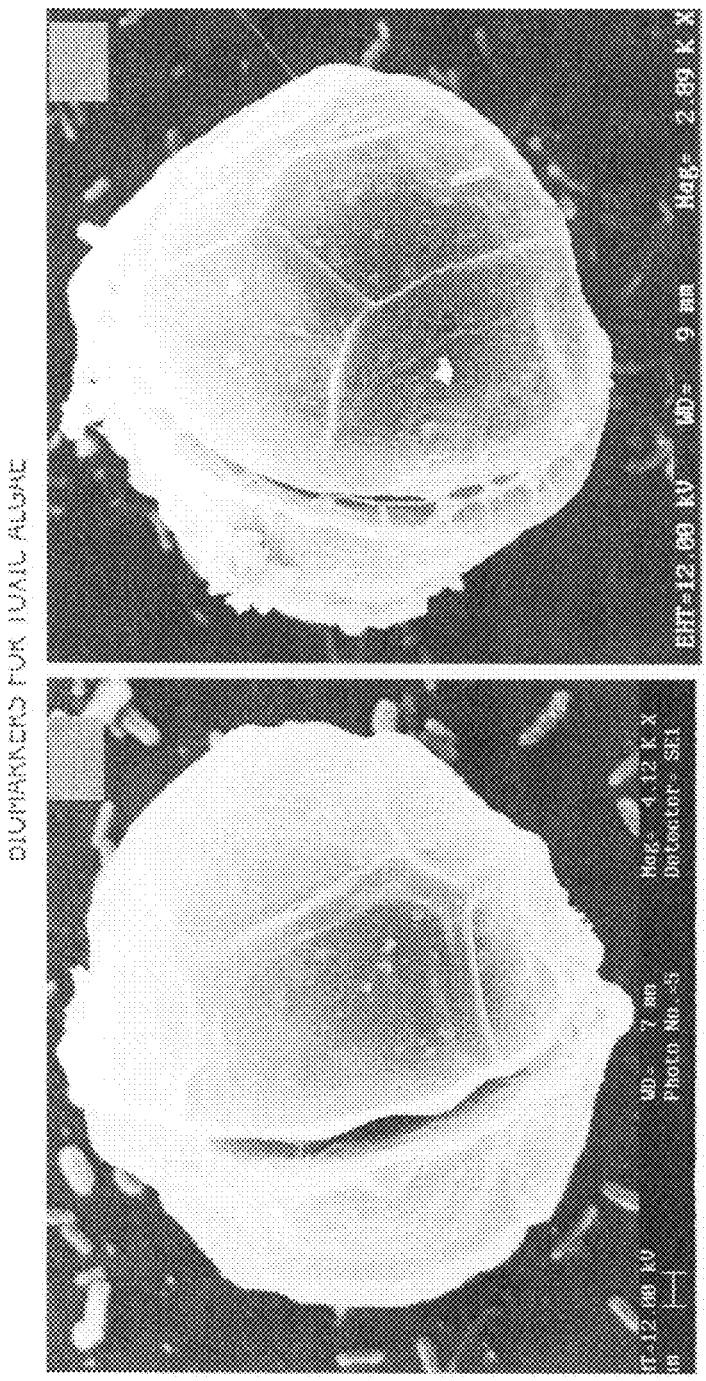
FIG. 1 contains scanning electron micrographs that show the minimal and insignificant variation in morphological features between toxic (panel A, strain AMKS2) and non-toxic (panel B, strain AMTK3) strains of the algae *A. minutum*.

In addition to exploring which algae express toxins and when such expression occurs, researchers have also examined the purpose(s) for which toxins are expressed. Wang & Hsieh [16] reported that toxins were produced as secondary metabolites when growth conditions become undesirable. According to the work of Taroncher-Oldenburg et al. [17] on a toxic dinoflagellate *A. fundyense*, it was found that toxin biosynthesis is coupled to the G1 phase of the cell cycle. They also found that observed variations in toxin content were a result of increasing periods of biosynthetic activity. Due to the harmful effects of cyclic perhydropurine saxitoxin (STX) production on humans and the environment, much work has been done on the ecology and physiology of STX biosynthesis in several PST-producing causative algal agents as well as on monitoring and predicting outbreaks of blooms in coastal waters caused by these organisms. However, the molecular mechanism involved in toxin biosynthesis is virtually unknown. Studies using labeled precursors with *Alexandrium tamarense* and *Aphanizomenon flos-aquae* have indicated that PST toxins are derived from acetate, arginine, and methionine [18]. Several speculative pathways have been suggested for the biosynthesis of these unique tricyclic perhydropurine derivatives. Oshima [19] has found the enzymes N-sulphotransferase and N-oxidase, which are reportedly involved in part of the PST biosynthetic pathway, in several dinoflagellates. However, direct precursors and specific enzymes have not been identified as yet and the full biosynthetic pathway for STX remains unresolved [20]. Toxin content is generally high in the exponential growth phase, but decreasing as cultures reach stationary phase. Low temperature and low phosphate concentrations both result in increased cell toxicity, N limitation may cause a decrease in toxicity [15]. These studies describe general patterns of dinoflagellate toxicity, but the physiological or biochemical mechanisms underlying the observed variations remain unknown.

In some embodiments, the present invention provides methods and materials for the detailed study of which proteins are related to toxin biosynthesis in various growth conditions and algal strains. Proteomic analysis can monitor expression of multiple proteins simultaneously. By comparing proteome expression of different stages of a toxic dinoflagellate and relate that to toxin production, proteins related to the toxin production can be found. Therefore, embodiments of the present invention represent important new tools for studying the physiological and toxicological ecology of toxic dinoflagellates by uncovering the molecular mechanism involved in the complex toxin biosynthetic pathway. Additional embodiments of the invention provide methods for detecting the presence of PST and particular species and strains of algae.

Various embodiments of the invention use a variety of detection and analysis techniques for polypeptides and nucleic acids that are known to those with skill in the art. For example, in some embodiments, nucleic acids that contain some portion of sequence that is algal in origin are analyzed using nucleic acid microarrays. These arrays were developed in the early 1990s to assist with the mapping of the human genome by speeding up the process of genome sequencing. Briefly, a microarray consists of up to thousands of DNA oligonucleotide probes fixed to a solid support in a sequential manner, each probe in a specific location on the solid support. The probes are usually synthesized directly on the substrate support material and are used to interrogate complex RNA or message populations based on the principle of complementary hybridization. A sample of nucleic acid containing a mixture of various sequences can be labeled and allowed to hybridize with the DNA probes of the microarray. After removal of partially hybridized and unhybridized nucleic acids, the presence of nucleic acids with sequences complementary to the sequences of probe DNAs can be detected via their labels. By the positions of the labeling on the array, the identity of the hybridizing nucleic acids can be ascertained. Microarrays thus provide a rapid and accurate means for analyzing nucleic acid samples. They can be used to detect trace amounts of nucleic acids and to distinguish between nucleic acids differing by as little as a single base, in thousands of samples simultaneously. Microarray technology has been used in the laboratory for RNA detection, nucleic acids sequencing projects and for analyzing transcription profiles of cells and tissues (Lichter, P et al. (2000) *Semin Hematol* 37:348-357; Tusher, V G et al. (2001) *Proc Nat Acad Sci* 98:5116-5121; Cook, S A and Rosenzweig, A. (2002) *Circ Res* 91:559-564; each one of which is hereby incorporated by reference in its entirety). Microarray technology is used in some embodiments of the invention to quickly screen and identify particular nucleic acids in biological samples comprising biological material from algae.

To create new methods of studying, classifying and identifying both species and strains of algae, including algae that produce toxins, the protein expression profiles of algae were examined. The present invention is based on the discovery of biomarkers which can be used to easily distinguish between algae of different strains and species. These biomarkers can be considered as "taxonomic biomarkers" to distinguish strains within the same species or between species and/or as potential "toxin biomarkers" for which expression was correlated to different toxin production patterns in *A. minutum*. With regards to different strains of *A. minutum*, as detailed below in the Examples section, our results showed that variations in morphological features between clones were minimal and not significant. However, strain-specific protein profiles with respect to toxic and non-toxic strains of *A. minutum* were obtained by two dimensional gel electrophoresis (2-DE) analysis. In some embodiments of the invention, features of the protein profiles represent the potential taxonomic biomarkers for strain and species differentiation and toxic biomarkers for the detection of toxin. Initial studies revealed that the expression pattern of T1, a unique protein found in a toxic strain, in relation to different phases of the growth cycle and physiological conditions, was tightly correlated to toxin biosynthesis in the examined algae. In some embodiments of the invention, the expression pattern of T1 can be used as a biomarker to study the toxin biosynthetic mechanism in toxic dinoflagellate cells. In additional embodiments, T1 is used as a toxin biomarker whose detection indicates the presence of toxin in a sample. Particular embodiments of the invention feature methods for the in depth study of toxin biosynthesis and metabolism in *A. minutum* and other phytoplankton. For example, some embodiments of the invention feature protein array technology to study and detect toxin biosynthesis in algae.

Various embodiments of the invention feature a variety of protein analysis and detection technologies. In some embodiments, for example, protein array technology is used to achieve high-throughput analysis of biological samples containing peptides. Protein arrays can be used to detect the presence of a known protein in a sample as well as discover peptides, proteins and compounds that interact with a known protein. Some embodiments of the invention use protein array technology to detect algal proteins in biological samples. Additional embodiments of the invention use protein array technology to screen and isolate biological samples for compounds that interact with an algal protein. In some embodiments, the interacting compound is a peptide. In some embodiments, the algal protein is a peptide comprising an amino acid sequence from the T1 biomarker protein. Techniques and strategies for the use of protein arrays are known to those with skill in the art. (For a review, see MacBeath G. et al. (2000) *Science* 289:1760-3.)

As shown below in the Example section, we have successfully identified and isolated proteins which have the potential to serve as taxonomic biomarkers for algal species or clone differentiation and as a toxin bio-indicator to study the PST biosynthetic pathway and detect the presence of toxin. The protein profiles of different clones of algal species were very similar confirming that they are the same species despite the discrepancy in their toxin profiles. Also, the differential expression patterns of toxic clones were unique and readily discernable from the non-toxic clones. Embodiments of the present invention will lead to the identification and characterization of strain- or species-specific proteins and will advance the development of fast and specific immunological procedures to identify nuisance and toxic marine phytoplankton species such as development of whole-cell immunofluorescence assay. An approach described in the following examples, of identifying toxin-related proteins using a combination of N-terminal Edman sequencing, MALDI-TOF MS analysis of tryptic digests based on protein spots isolated from 2D-PAGE, 3' RACE cloning as well as physiological verification, also serves as a blueprint for similar work with other toxic species in the future.

Definitions

Unless defined otherwise, technical and scientific terms used herein have the same meaning as commonly understood by one of ordinary skill in the art to which this invention belongs. One skilled in the art will recognize many methods and materials similar or equivalent to those described herein, which can be used in the practice of the present invention. Indeed, the present invention is in no way limited to the methods and materials described. For purposes of the present invention, the following terms are defined below.

As used herein, the term "biological material" refers to a sample of matter in which some portion of the material is biological in nature. In some embodiments of the invention, the material originates in the tissues of a living organism. In other embodiments, the material is synthetic but comprising carbon-based organic compounds. Additional embodiments feature polypeptides and polynucleotides comprising naturally occurring and/or artificial, non-naturally occurring amino acids and nucleotide bases.

"Material from an alga" refers to a substance or a molecule that at one time was part of or synthesized by an organism classified as an alga. This material may have been obtained directly from an algae sample. Alternatively, the material may be present in non-organismal media, such as a suspension or buffer. Additionally, "material from an alga" also refers to a substance or a molecule that at one time was part of or synthesized by an organism classified as an alga which is now part of, internalized within or associated with another organism and that retains some part of the sequence, structure or activity that the substance or molecule had when part of or synthesized by the alga.

"Biomarker" refers to a biological substance which serves to provide classification information regarding the species or strain of an alga and/or serves to indicate the presence or absence of another substance which is a "material from an alga" (see above). In some embodiments of the invention, the biomarker is a proteinaceous or nucleic acid-based compound synthesized by a particular species or strain of algae for at least some portion of the life cycle of the algae under at least one set of conditions.

An "aquatic organism" is any form of unicellular or multicellular life that exists for a least some part of its lifespan within an aquatic environment. In some embodiments of the invention, "aquatic organism" refers to an organism that spends a minority of its lifespan in an aquatic environment. In some embodiments, avian life forms that contact aqueous environments and/or any organisms that are associated with aqueous environments are considered to be aquatic organisms.

"2-DE" refers to the separation of molecules in more than one dimension, e.g. the separation of a mixture of molecules by more than one differing characteristic of the molecules in the mixture. In some embodiments, "2-DE" refers to the separation of proteins and peptides through gel electrophoresis, wherein the molecules are distinguished by molecular size and by pH/isoelectric point characteristics. In other embodiments, molecules are distinguished by the technique using either molecular size or pH/isoelectric point plus some other characteristic. In additional embodiments, two or more characteristics other than molecular size or pH/isoelectric point are used.

EXAMPLES

Materials and Methods

Unless stated otherwise, all chemicals were purchased from Sigma (USA). All solvents were at least of AR grade while most were of HPLC grade.

1. Cultivation of *Alexandrium Minutum*

1.1. Experimental Cultures

Non-axenic cultures of eight clones of the dinoflagellate *A. minutum* including 5 toxic (AMKS2, AMKS3, AMKS4, AMTK4 and AMTK7) and 3 non-toxic (AMTK3, AMTK5 and AMTK6) strains were obtained from the Institute of Fisheries Science, National Taiwan University, Taipei 10617, Taiwan, ROC. The strains of AMTK and AMKS of *A. minutum* were isolated from the TungKang (TK) and Kaohsiung (KS) areas of Taiwan respectively. These unialgal isolates were batch cultured in K medium [23] at 20° C. under a 12:12 hr light: dark photoperiod at a light intensity of approximately 100-150 μmol photons m-2 s-1 provided by fluorescent lamps in a Conviron growth chamber (Model S10H, Conviron Controlled Environments, Winnipeg, Canada) for fourteen days until the mid-exponential growth phase was reached.

1.2. Investigation of Two Representative Strains of *A. Minutum* Over a Five-Day Period, and Also Grown Under Nutritional and Environmental Stresses AMKS2 and AMTK3 were selected to represent the toxic and non-toxic strains of *A. minutum* respectively and were examined over a five-day period as well as under light-, nitrogen- or phosphate-limited balanced growth to find a set of candidate proteins which may be concurrent with the PST toxin production patterns. Axenic cultures of toxic and non-toxic strains of *A. minutum* were also generated to exclude the potential contamination caused by bacterial proteins on the expression of these candidate proteins.

1.2.1. Investigation of *Alexandrium Minutum* over a 5-Day Period

Batch cultures of AMKS2 (toxic strain) and AMTK3 (non-toxic strain) of *A. minutum* were prepared by inoculating 1 litre of exponentially growing cultures into 10 litres of K medium and were grown as described in Section 2.1.1. Cultures of *A. minutum* were synchronized by a dark-induced block/release method [17]. Synchronization of the experimental cultures was achieved by maintaining the cells in continuous darkness for 72 hours. The cells were then entrained to the same photoperiod regime of 12L/12D as light was turned on and the first sample was collected immediately at 8 a.m. of Day 1. These representative cultures were sampled over a 5-day period at circadian times separated by 12 h (i.e. 8 a.m. and 8 p.m. everyday) since *A. minutum* grew at the rate of 0.20 divisions d-1 in optimal environmental and nutritional conditions [24].

1.2.2. Investigation of *Alexandrium Minutum* Grown Under Nutritional and Environmental Stresses The cultures at different conditions were prepared as previously reported [24] and briefly described below:

A. The "seed population" was concentrated by centrifugation at 1,000×g for 15 minutes at 22° C. (himac CR 22f, Hitachi High-Speed Refrigerated Centrifuges, Japan) at the mid log of the exponential growth phase (about Day 14) and the pellets were rinsed twice with sterilized seawater to avoid any carry-over of nitrogen, phosphorous or inhibitors in the inoculum.

B. The light-limited cultures were prepared by inoculating the "seed population" into normal K medium to achieve an initial cell density of 1×106 cells L-1 and were maintained in continuous darkness for 72 hours.

C. The nitrogen-limited and phosphorous-limited cultures were prepared by inoculating the "seed population" into nitrogen-limited and phosphate-limited K medium respectively to achieve an initial cell density of 1×106 cells L-1 and the cultures were incubated at normal dark/light photoperiods. The cell densities were constantly monitored until the stationary phase was reached. The purpose of using stationary phase cultures was to ensure that all carry-over of nitrogen and phosphorus in the inoculum had been used up and the growth was limited either by phosphate or nitrate.

D. Axenic culture of strains of AMKS2 and AMTK3 of *A. minutum* were established by inoculating the cells into the culture medium which was supplemented with antibacterial mixtures of 100 units/ml penicillin and 100 μg/ml streptomycin (GIBCO BRL antibiotics, Cat. No. 15140-122, 100 mL) for several generations and mass cultures for analysis were made by growing the cells in 5 L flask with 3 L of K medium supplemented with antibacterial mixtures as mentioned above.

2. Preparation of Extract for Proteomic Analysis and HPLC-FD Analysis

Approximately 1×10$^6$ *A. minutum* cells were collected by centrifugation at 5,000×g for 20 minutes at 22° C. (himac CR 22f, Hitachi High-Speed Refrigerated Centrifuges, Japan) and the pellets were rinsed twice with sterilized seawater to avoid any carry-over culture medium. The pelleted cells were then kept in a −80° C. ultra-low freezer for subsequent analysis. No sample was stored for more than 3 months.

2.1. Protein Extraction and Quantification

Water-soluble proteins were isolated as previously described [22]. Briefly, with a Mircotip-probe sonifier (Model 250, Branson Ultrasonics, Danbury, Conn., USA), cells were lysed in 0.5 mL of 40 mM pre-chilled (4° C.) Tris buffer at pH 8.7 containing 30 units of endonuclease (benzonase isolated from S. marcescens, Sigma E8263). Cell debris and unbroken cells were removed by centrifugation at 22,220×g for 15 min at 4° C. (Mikro 22R, Hettich, Germany). The supernatants were concentrated by ultrafiltration through an Amicon YM-3 membrane (Amicon, Bedford, Mass., USA) following the manufacturer's instructions. The extracts were then applied to a Micro BioSpin 6 Column (Bio-Rad, Hercules, Calif., USA) previously equilibrated with a Tris buffer (10 mM Tris-HCl, pH 7.4) containing 0.02% sodium azide following the manufacturer's instructions. Flow through from the column was collected.

2.2. Toxin Extracts from Cultures of Dinoflagellate *Alexandrium Minutum*

The pelleted cells were homogenized in 0.03M glacial acetic acid with a Mircotip-probe sonifier (Model 250, Branson Ultrasonics, Danbury, Conn., USA). Samples were chilled on ice between bursts of less than 10 seconds. Cell debris and unbroken cells were removed by centrifugation at 22,220×g for 15 min at 4° C. (Mikro 22R, Hettich, Germany). The supernatants were filtered with a molecular-sieve membrane with a 10,000 Dalton cutoff (Amicon YM-10 membrane, Amicon, Bedford, Mass., USA) following the manufacturer's instructions. The analytical procedures as described by Oshima [19], for quantification of analogues of STX: gonyautoxin I, II, III, IV (GTX1-4) were used. This methodology involved the use of a post-column high performance liquid chromatography (HPLC) derivatization coupled with fluorescence detection. The HPLC system was from Waters Corporation, USA. A stainless-steel column of reversed phased packing (Inertsil C8, 3 u, 150 mm×4.6 mm and Inertsil C8, 5 u, 7.5 mm×4.6 mm all-guard cartridge, Alltech, USA) was used. 7 mM periodic acid in 50 mM potassium phosphate buffer (pH9.0) was used as the oxidizing reagent and 0.5M acetic acid as the acidifying reagent. To achieve the separation of closely related toxin peaks, an isocratic elution with a mobile phase of 2 mM sodium 1-heptanesulfonate in 10 mM ammonium phosphate (pH 7.1) was used. GTX1/4 and GTX2/3 standards were purchased form the National Research Council of Canada (NRC). The detection limits for individual toxins were determined to be: 17 ng for GTX1; 4 ng for GTX2; 4 ng for GTX3; 10 ng for GTX4. Variability was found to be less than 10%. A 60-72% recovery was usually found. Concentrations were not corrected for recovery rates.

3. 2-DE

40 μg or 150 μg of each sample was mixed with a rehydration buffer before being loaded onto IPG strips of linear pH gradient 4-7 (Amersham Biosciences, Hong Kong, China) for subsequent staining with silver or Coomassie Brilliant Blue R-250 respectively. Rehydration, isoelectric focusing and equilibration were performed as previously described [22]. Subsequently, SDS-PAGE was performed and proteins on the 2-DE gels were (1) visualized by silver staining for pattern comparisons; (2) electro-transferred onto a PVDF membrane for N-terminal sequencing and (3) staining with Coomassie Brilliant Blue R-250 for MALDI-TOF mass spectrometry. Three 2-DE gels were performed for each condition. Unless stated otherwise, the 2-DE gels shown are representative of the 3 gels performed. Protein spots were selected for quantitative analysis if they have the potential to serve as a biomarkers, either taxonomic or toxin, and were consistently visible in all samples from one condition. The density of each spot was measured using an ImageScanner (Amersham Biosciences, Hong Kong, China) equipped with ImageMaster software from Amersham Biosciences (Hong Kong, China). The abundance of each spot was calculated as a percentage of the total density of all 626 spots measured on each gel.

FIGS. 3 and 4 show the 2-DE differential protein expression profiles for toxic and non-toxic algae. In these experiments the IEF of the first dimension was over a pH range of 4.0 to 7.0. The second dimension was a SDS-PAGE in a 15.0% polyacrylamide gel.

4. MALDI-TOF Mass Spectrometry and N-Terminal Amino Acid Sequencing By Edman Degradation Protein spots were selected to determine the peptide mass fingerprinting by a MALDI-TOF mass spectrometer (MS) (Autoflex, Bruker Daltonics, Germany) if they have the potential to serve as a "taxonomic biomarker" or "toxin biomarker" and were consistently visible in all samples from one condition. 150 μg of proteins separated by 2-D PAGE were digested in gels according to the method described by Shevchenko and coworkers [25]. The digests were desalted with Zip Tip (Millipore, Boston, Mass., USA) and subjected to analysis by MALDI-TOF MS. Calibration of the instrument was performed with internal standards, namely angiotensin, substance P, bombesin, trypsin autolysis fragment, and adrenocorticotropic hormone with the respective monoisotopic masses at 1046.5 m/z, 1347.7 m/z, 1620.8 m/z, 2211.1 m/z, 2465.1 m/z. Monoisotopic peptide masses were assessed to the peptides examined and database searches were performed with the "Protein Warehouse Program" provided by Bruker against SWISS-PROT and TrEMBL databases. The search was limited to sample spots with corresponding molecular weight and pI range with a mass tolerance of +/−0.2 Da. One missed cleavage per peptide was allowed and cysteines were assumed to be carbamidomethylated with acrylamide adducts and methionine in oxidized form.

Unidentified proteins were further characterized by N-terminal sequencing. Proteins separated by 2-D PAGE were electro-transferred onto PVDF membranes. The PVDF membrane-bound proteins were visualized by staining with 0.1% Coomassie Brilliant Blue R-250 in 50% aqueous methanol for 2 min, and destained in 40% methoanol and 10% acetic acid. Selected protein spots were excised and subjected to amino acid sequencing by Edman degradation, using a Procise 492 cLC Model 610A protein/peptide sequencer (Applied Biosystems, Hong Kong, China). Amino acid sequences obtained were searched either against the Protein DataBank (PDB) or SWISS-PROT by BLAST. Settings for querying short sequences for nearly exact matches of peptide were used.

Example 1

Figure 2:
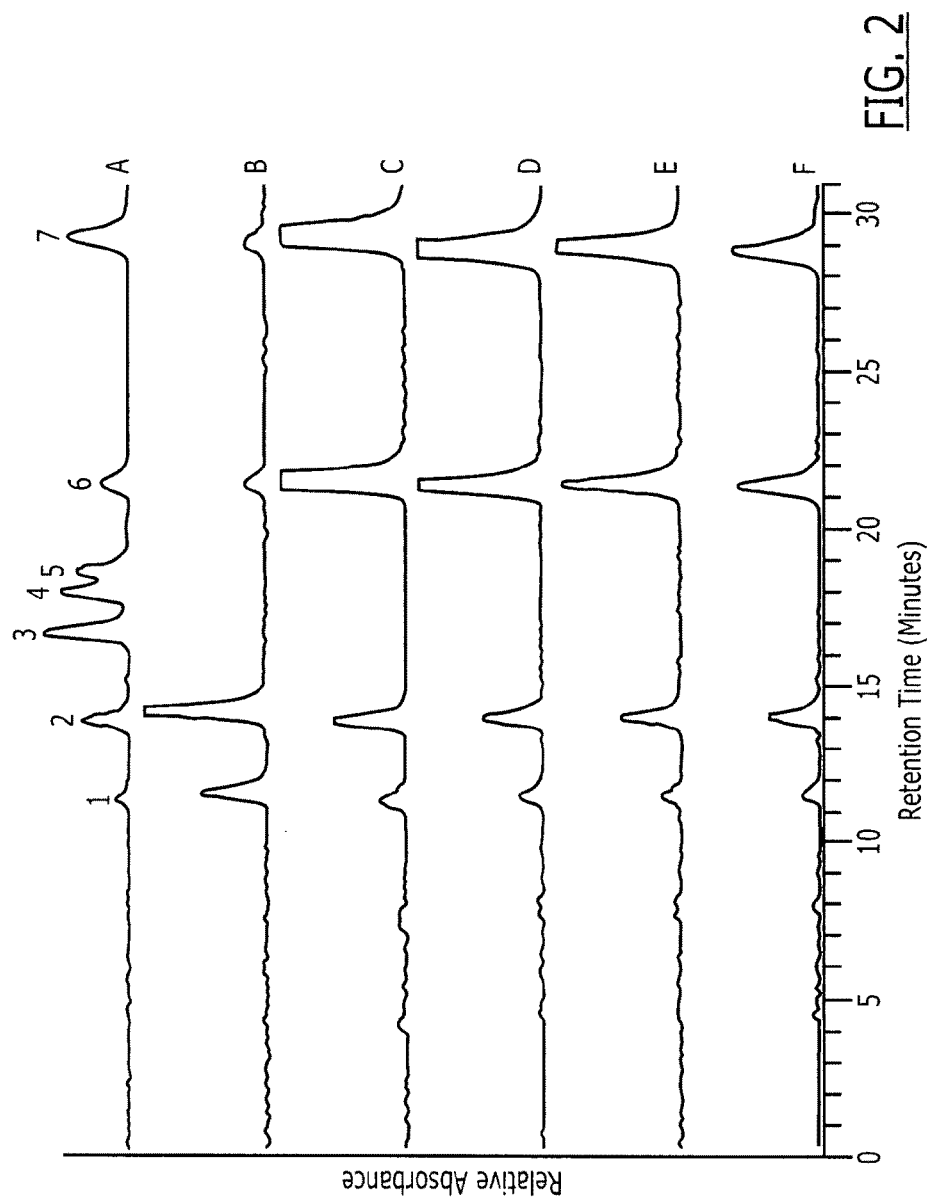
FIG. 2 shows high performance liquid chromatograms (HPLC) of paralytic shellfish poisoning (PST) toxin profiles from various samples of *A. minutum* anal "fingerprint" has been suggested as a biochemical characteristic to distinguish strains within the Alexandrium species and could be regarded as a potential taxonomic biomarker [14]. However, Anderson et al [15] suggested that toxin composition is variable and reflects adaptations to nutritional and environmental conditions, and not a fixed genetic trait.

Morphology PST Toxin Profiles and Differential Protein Expression Patterns of *A. Minitum* Isolates Under Optimal Conditions Unialgal culture of eight clones of the dinoflagellate *Alexandrium minutum* were divided into two categories according to their toxicity namely toxic and non-toxic strains. Using Balech [26] as the standard of taxonomy of *Alexandrium*, the following characteristics, especially small cell size, narrow sixth precingular plate and wide posterior sulcal plate, indicated all these isolates were *A. minutum*. Variation in morphological features between the two categories was minimal and not significant (FIG. 1). The toxin components of different clones of *A. minutum* were assayed by HPLC-FD and found to be gonyautoxin 1-4 only (FIG. 2). These different strains of toxic *A. minutum* show a wide range of absolute toxicities: AMTK7, AMKS-2 and AMKS-3 are dominated by GTX-3 and GTX-2 with a small amount of GTX-4 and GTX-1, while AMTK4 contained trace and almost equal amounts of GTX-3 and GTX-2 in addition to the two major toxins GTX-4 and GTX-1. AMKS-4 contained small amount of GTX-4 and GTX-1 and medium amounts of GTX-3 and GTX-2 when compared with other clones. On the other hand, strains AMTK-3, AMTK-5 and AMTK-6 were found to be consistently nontoxic.

Figure 3A:
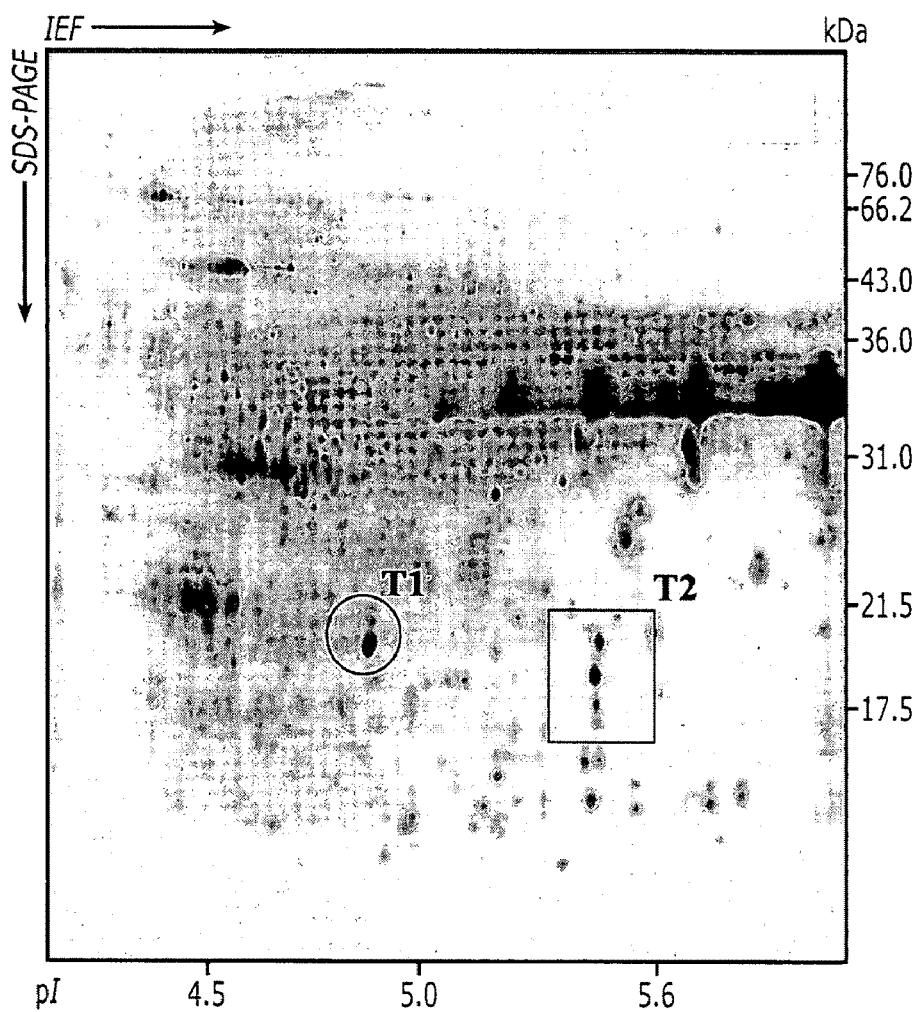
Figure 3B:
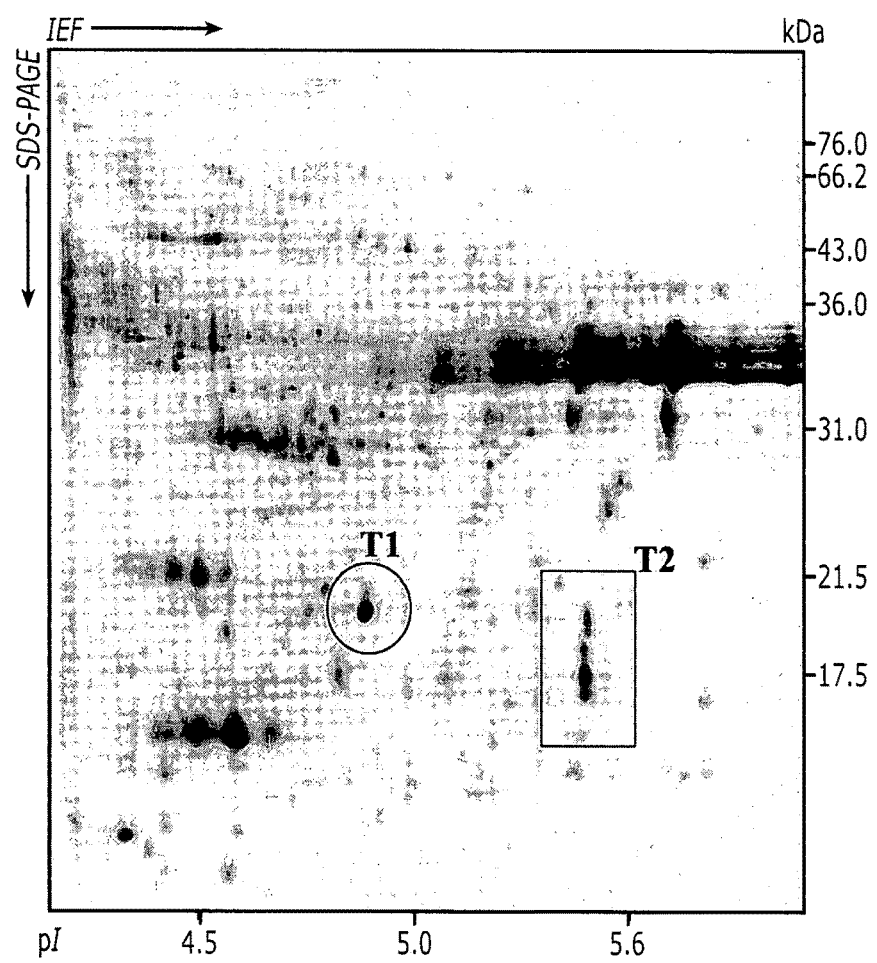
Figure 3C:
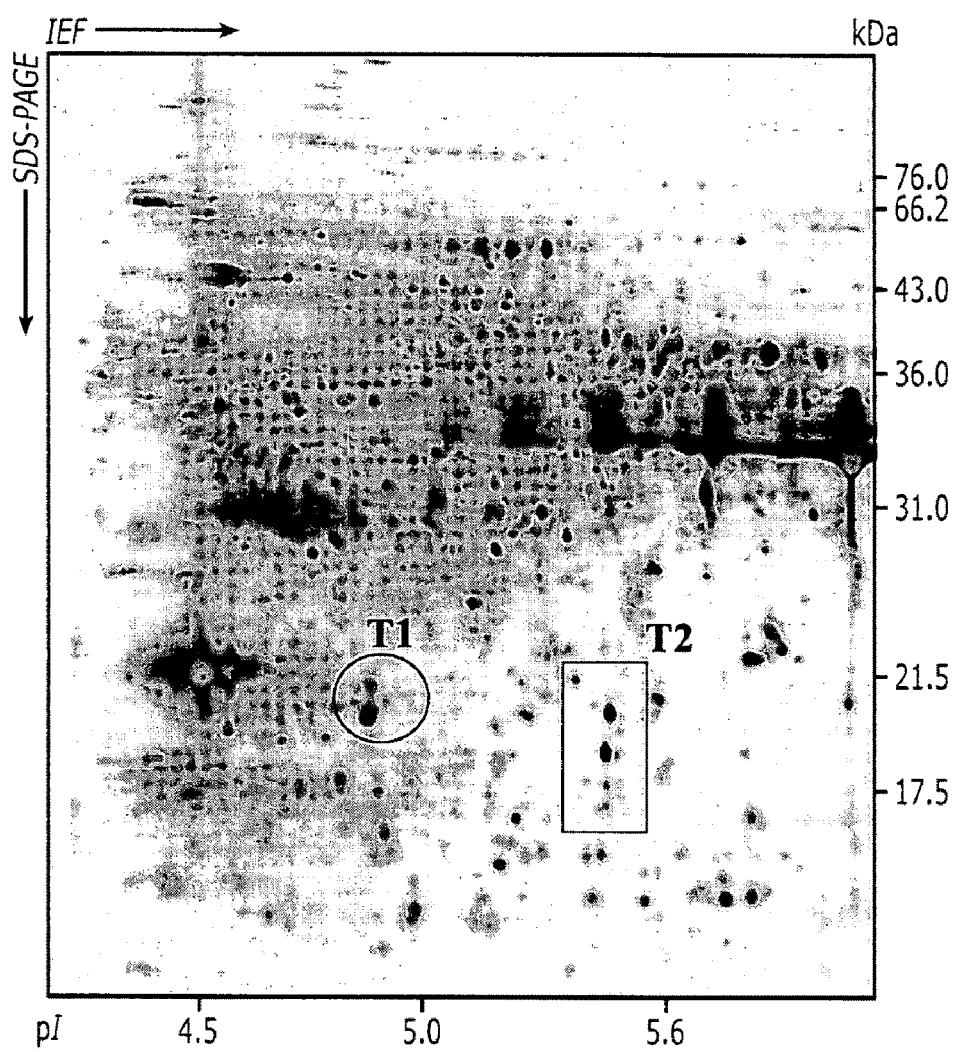
Figure 3D:
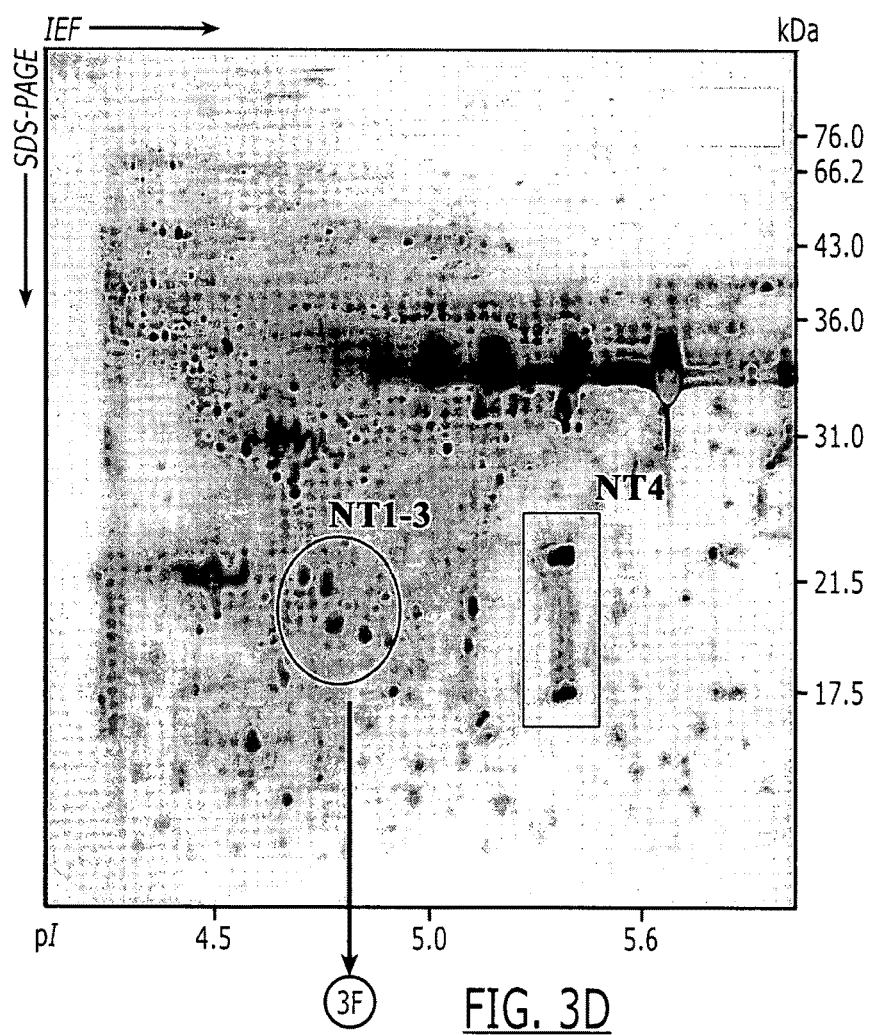
Figure 3E:
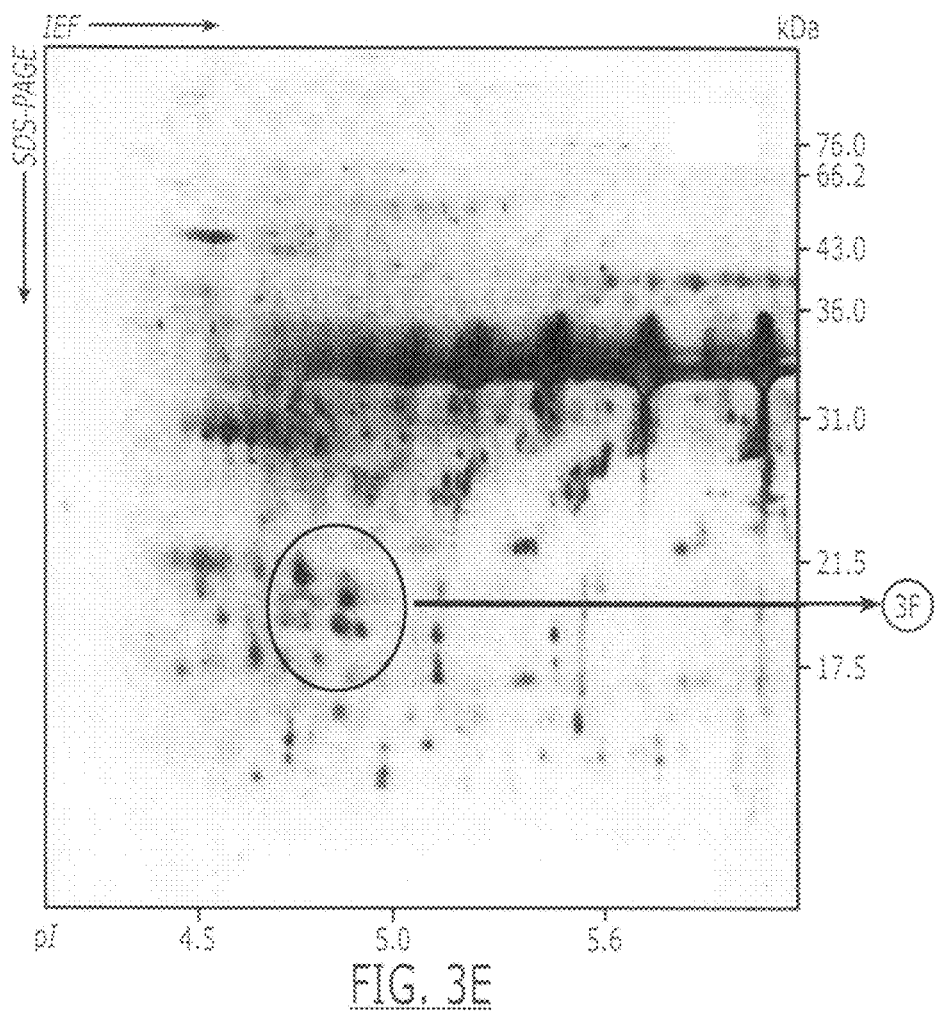
Figure 3F:
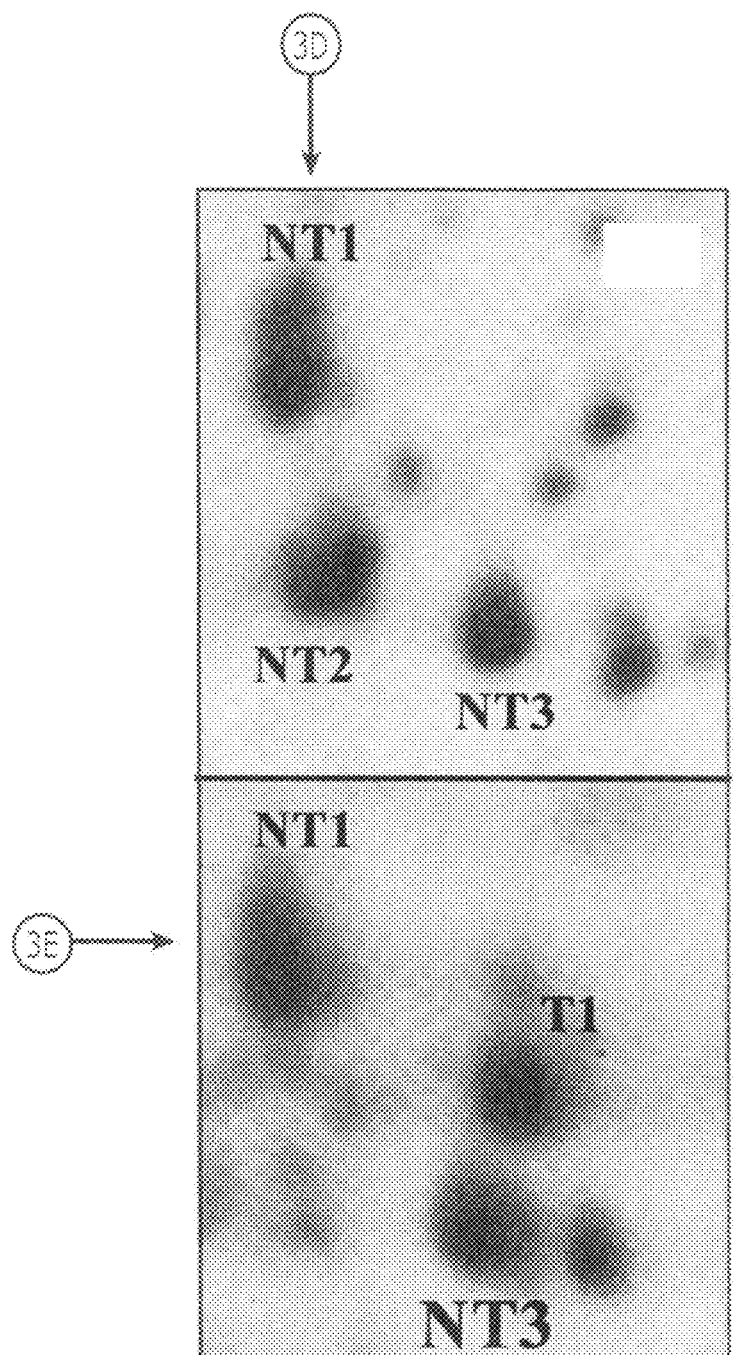

Proteome reference maps were established for the toxic as well as non-toxic strains of *A. minutum*. In general, we found strong similarities in gel patterns of the arrayed proteins between the strains of the same category, toxic or non-toxic. 2-D gels of different clones of the same category grown under the same conditions were superimposable. Representative 2-D gels from toxic (FIGS. 3A to 3C) and nontoxic (FIG. 3D) strains of *A. minutum* are shown. A comparison of these 2-D maps illustrates that they shared a majority of proteins and the relative position of similarly grouped and shaped protein spots in gels of algae from both categories suggests the majority of the proteins have the same identity. However, significant differences were observed for several abundant proteins when comparing the gels for toxic and non-toxic algae. A unique abundant protein spot, T1 (with pI 4.9 and an apparent molecular mass of 20 kDa) and a cluster of proteins, T2 (with pI 5.5 and apparent molecular masses between 17.5 and 20 kDa), were consistently found in all toxic species (FIGS. 3A to 3C). On the other hand, in the proteome maps of non-toxic strains, several abundant proteins, NT1 (with pI 4.7 and an apparent molecular mass of 20 kDa), NT2 (with pI 4.7 and an apparent molecular mass of 19 kDa), NT3 (with pI 4.8 and an apparent molecular mass of 19 kDa) and a pair of proteins, NT4 (with pI 5.4 and apparent molecular masses between 17.0 and 22 kDa), were detected in the non-toxic strains only (FIG. 3D). Since the location and intensity of T1 and NT3 were very close, a composite gel (FIG. 3E) was obtained by applying equal amounts of water-soluble proteins of toxic and non-toxic strains. Regions enclosed by circles in FIGS. 3D and 3E are expanded in the upper and lower portions of FIG. 3F respectively. T1 and NT3 were confirmed to be two different protein spots with minute difference in apparent molecular masses and pIs. The separate identities of T1 and NT3 were also confirmed with a combination of MALDI-TOF MS, enzyme digestion and Edman sequencing for internal sequences.

2. Discussion

A commonly accepted paradigm in the study of saxitoxin-producing dinoflagellates is that the total concentration of all toxins (toxin content) in one isolate can vary with growth conditions, but that the relative abundance of each toxin (toxin composition) does not change [28]. The toxin profiles in the test alga were consistent when cells were grown in optimal environmental and nutritional conditions. Different strains of *A. minutum* can be distinguished by their unique toxin profiles (different relative abundance of each toxin) and the toxin profiles of different strains of *A. minutum* in this study, in which GTX2 and GTX 3 are major components, are similar to that of *A. minutum* strains from Australia [29] and Spain [30]. However, Anderson et al [15] working on *A. tamarense* showed conclusively that drastic changes in the relative abundance of the different PST analogues could occur in *Alexandrium* isolates in nutrient-stressed batches or semi-continuous cultures. Therefore, toxin profile "fingerprints" can no longer be regarded as potential taxonomic biomarkers to distinguish strains within the *Alexandrium* species. In the above example, proteomic analysis was carried out on 5 toxic and 3 non-toxic strains of *A. minutum* in order to search for taxonomic biomarkers for both categories (toxic and non-toxic) for strain differentiation. A comparison of the proteome reference maps generated for toxic and non-toxic strains revealed that variations in differential protein expression among toxic strains on one hand or among non-toxic strains on the other were minimal and not significant. However, pronounced differences in protein expression were seen when toxic strains were compared to non-toxic strains. Our results show that the toxic strains and the morphologically similar non-toxic strains can be distinguished by examination of their differential protein expression patterns on 2-DE gels (FIG. 3). Although toxic and non-toxic strains shared a majority of proteins, significant differences between the two catagories were seen in several abundant proteins, i.e. NT1 to NT4 in non-toxic strains and T1 to T2 in toxic strains. In this regard, 2DE analysis can detect the presence of strain-specific proteins for strain differentiation. The techniques demonstrated in Example 1 are useful for many applications, including research into the metabolism of harmful dinoflagellates, since these strain-specific proteins serve as taxonomic and toxic biomarkers that are not influenced by the physiological state of the cells.

Example 2

Dynamics and Differential Protein Expression Patterns of Saxitoxin Production of *A. Minutum* Under Different Growth Phases and Different Nutritional and Environmental Stresses In our study, the total culture toxin concentration closely followed the cell concentration, increasing throughout the entire experiment during exponential phase between Day 1 and Day 5 in optimal growth conditions. The total toxicity on Day 1, Day 3 and Day 5 is listed in Table 1 as AMKS2-1, AMKS2-3 and AMKS2-5 respectively. In N-limiting conditions (AMKS2-N), cells contained half as much toxin as those cultured under normal conditions (AMKS-1, AMKS-3 and AMKS-5). In contrast, toxin content in PO43-limited (AMKS2-P) and light limited (AMKS2-L) cultures increased significantly, compared with the nitrogen-limited culture (Table 1).

TABLE 1

Toxicity measurements of toxic strains of *A. minutum*

| Sample | Toxicity (pgSTXeq cell$^{-1}$) |
|---|---|
| AMKS2-1 | 1.91 |
| AMKS2-3 | 2.68 |
| AMKS2-5 | 2.94 |
| AMKS2-N | 1.12 |
| AMKS2-L | 3.09 |
| AMKS2-P | 3.04 |
| AMKS-AB | 2.35 |

Toxicity of toxic strain AMKS2 cultures harvested Day 1 (AMKS2-1), Day 3 (AMKS2-3) and Day 5 (AMKS2-5) in the exponential growth phase during a 5-day period in full K medium and under light-limited (AMKS2-L), nitrate-limited (AMKS2-N), phosphate-limited (AMKS2-P) and supplemented with antibiotics mixture of 100 units/ml penicillin and 100 µg/ml streptomycin (GIBCO BRL antibiotics, Cat. No. 15140-122, 100 mL) in balanced growth cultures (AMKS2-AB).

Figure 4A:
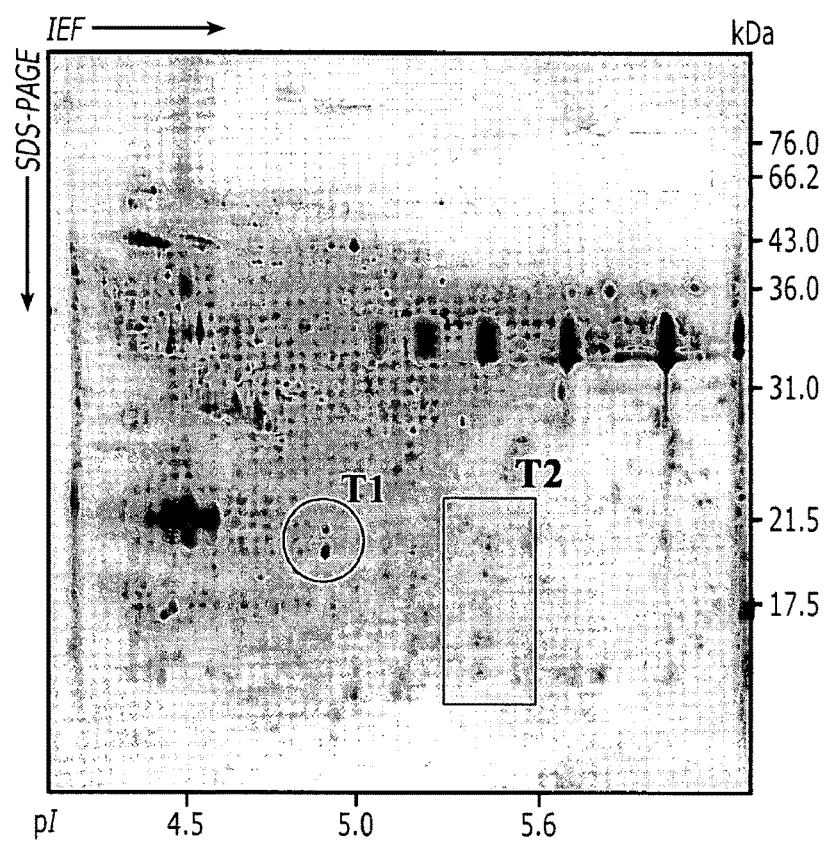
Figure 4B:
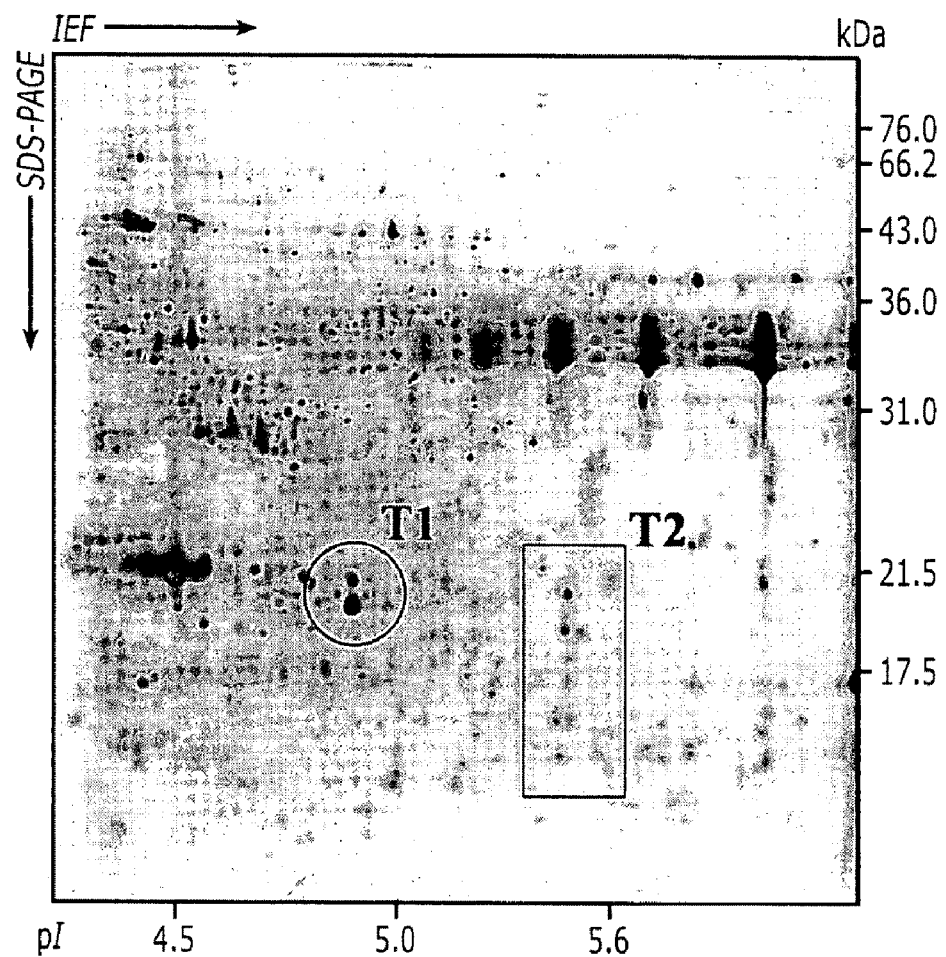
Figure 4C:
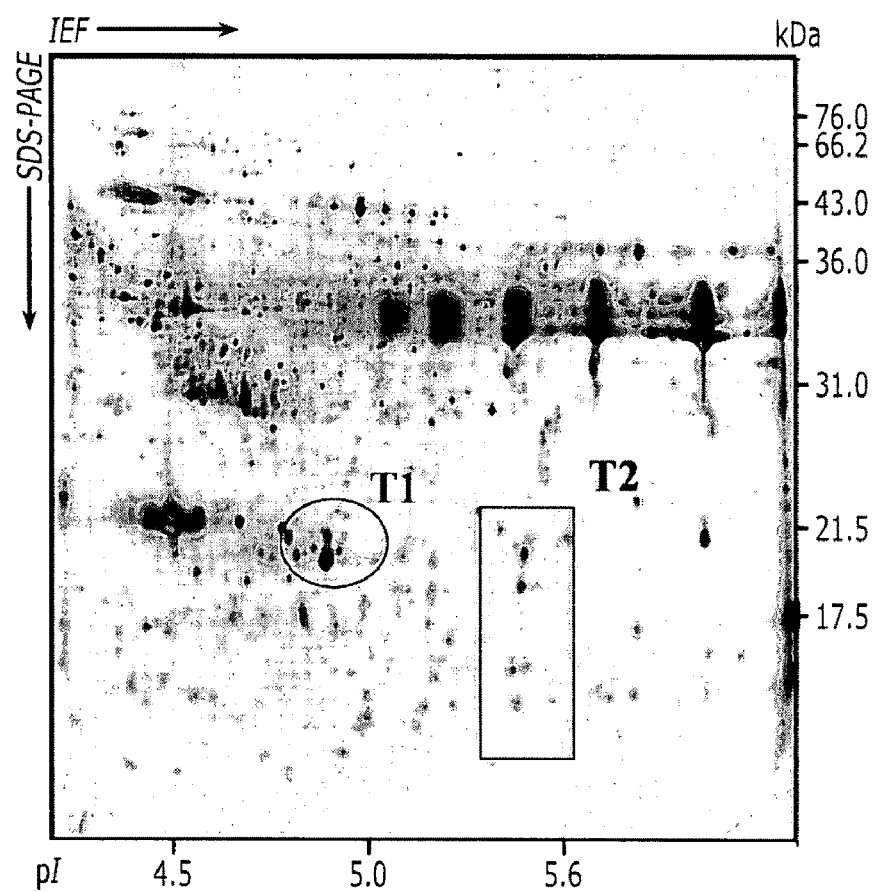
Figure 4D:
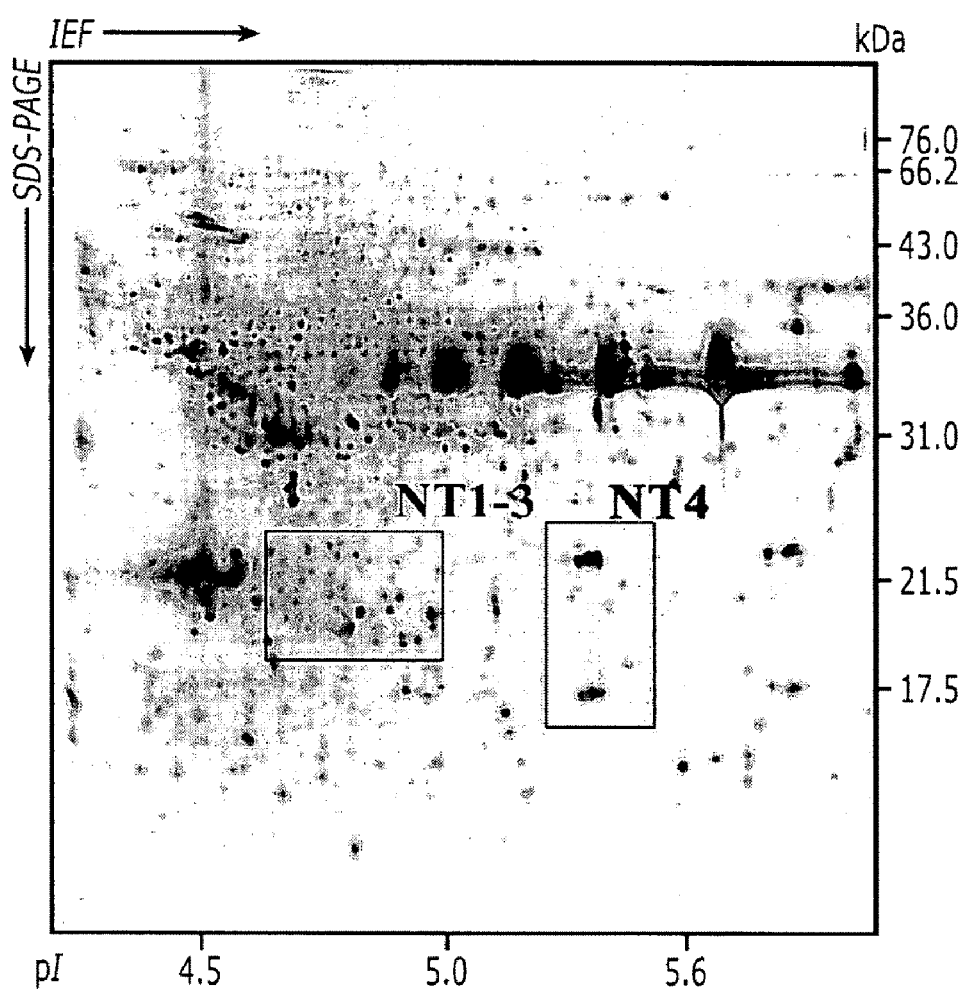
Figure 4E:
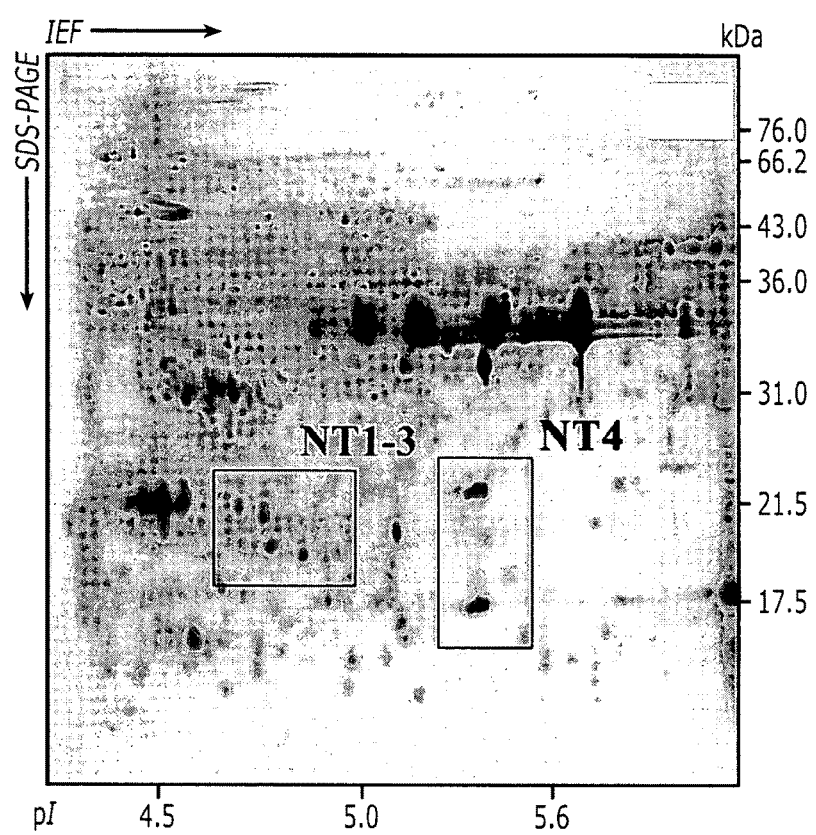
Figure 4F:
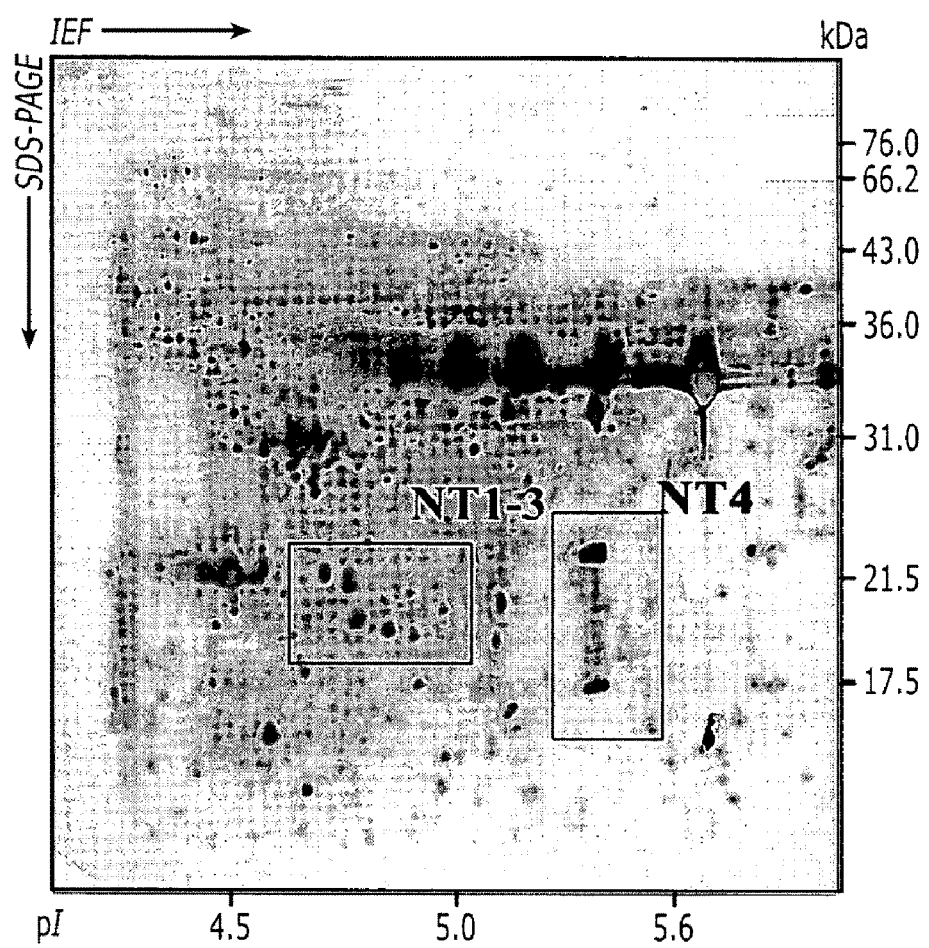
Figure 4G:
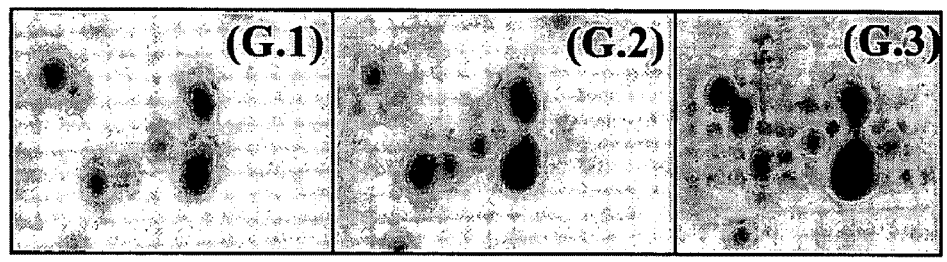
Figure 4H:
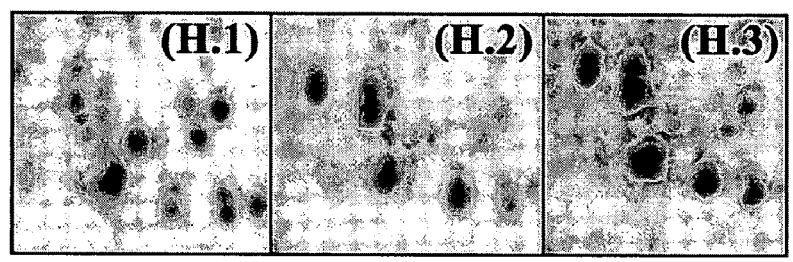
Figure 5A:
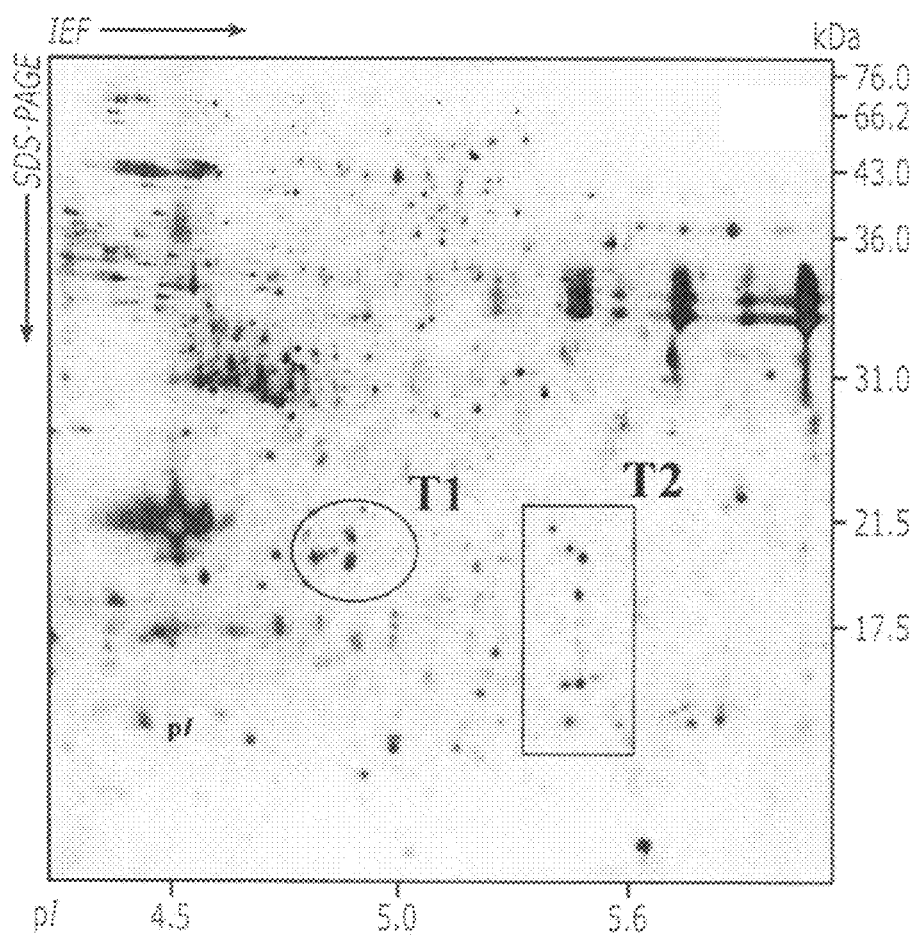
Figure 5B:
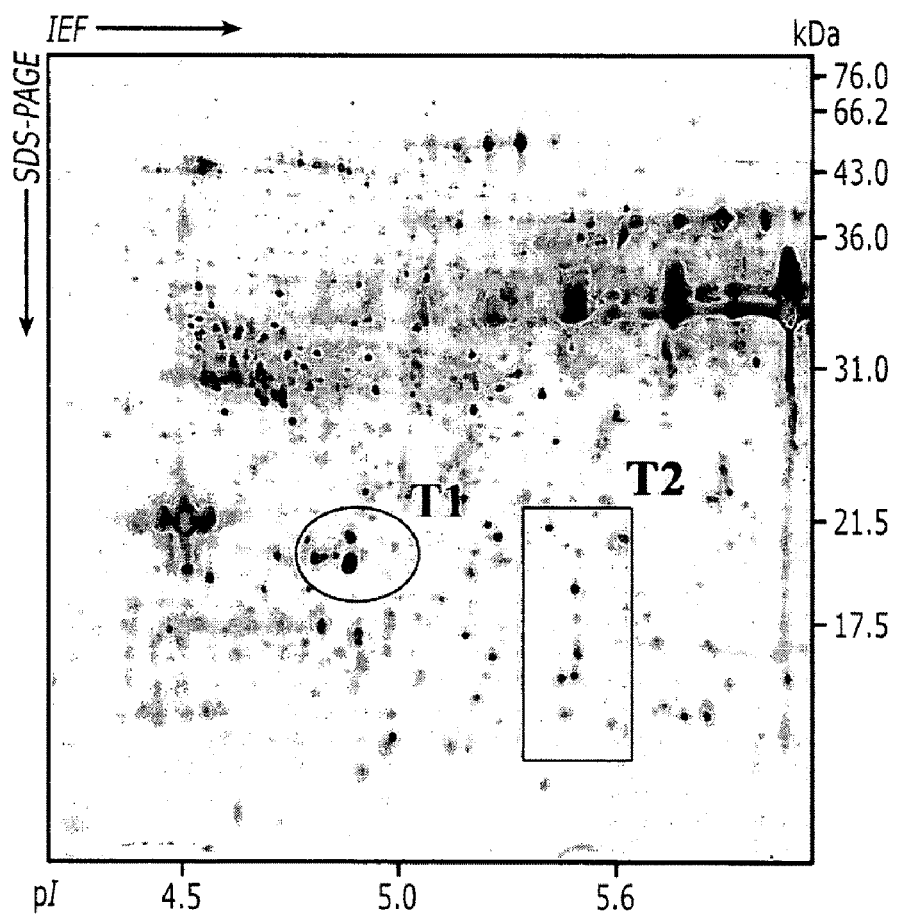
Figure 5C:
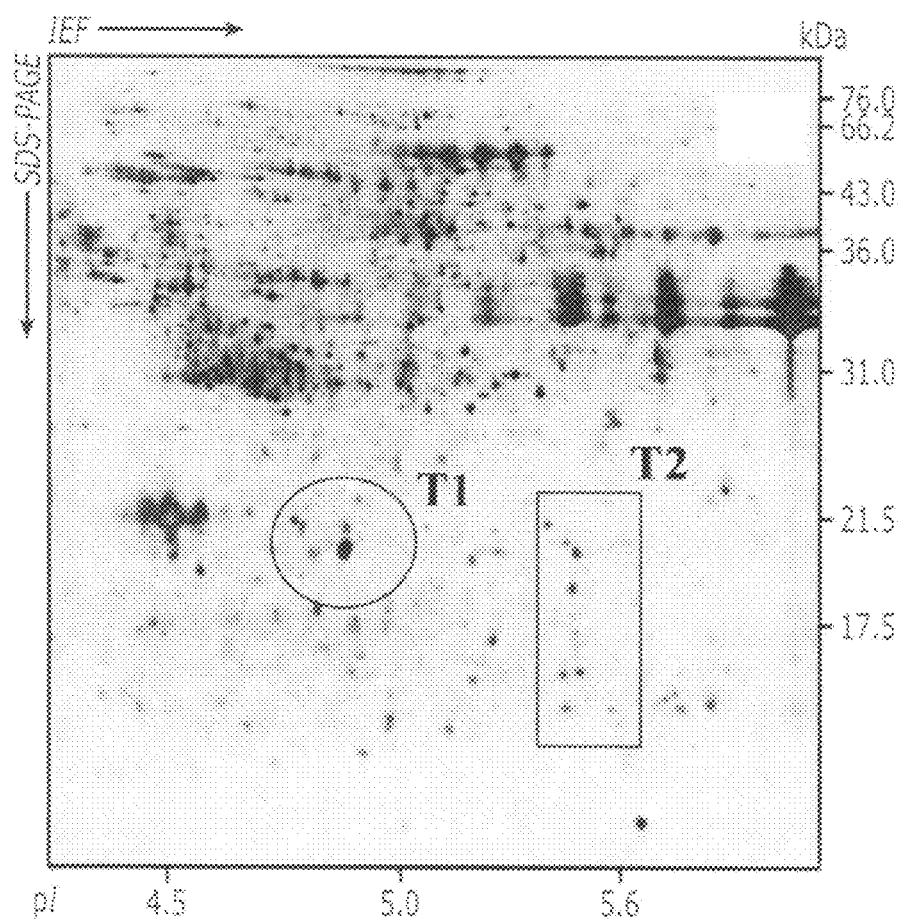
Figure 5D:
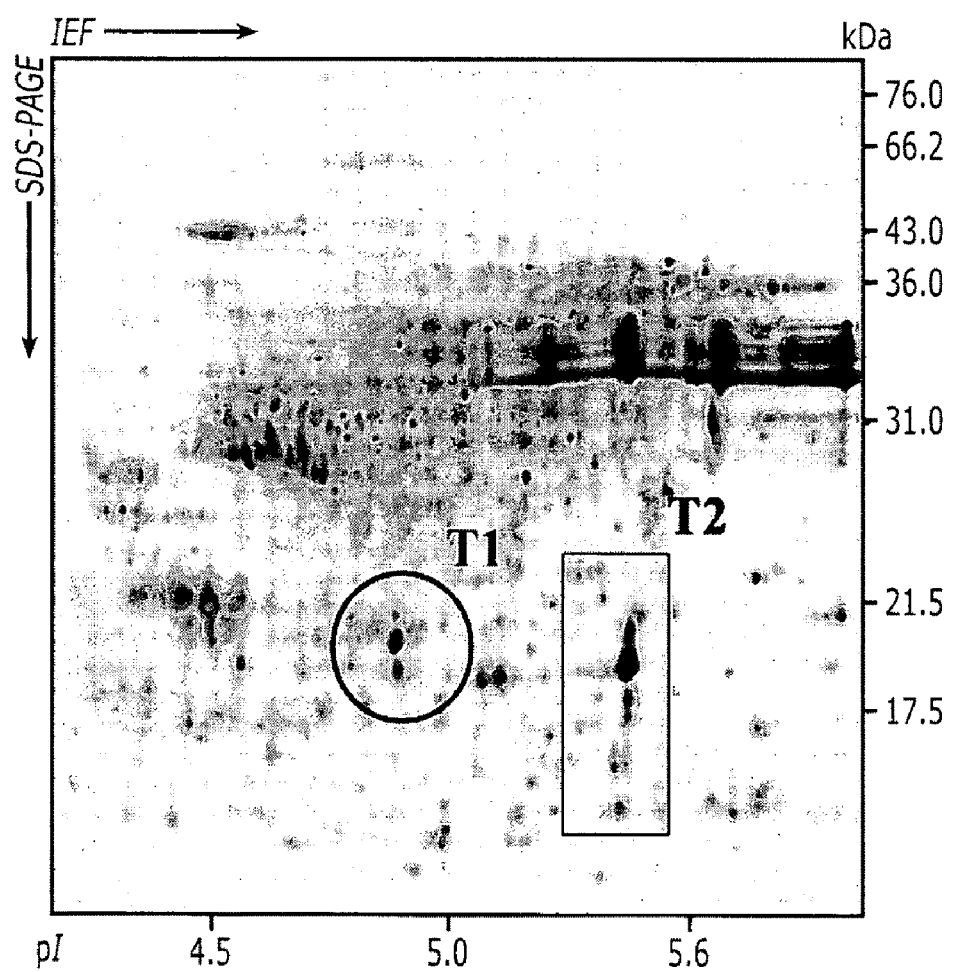
Figure 5E:
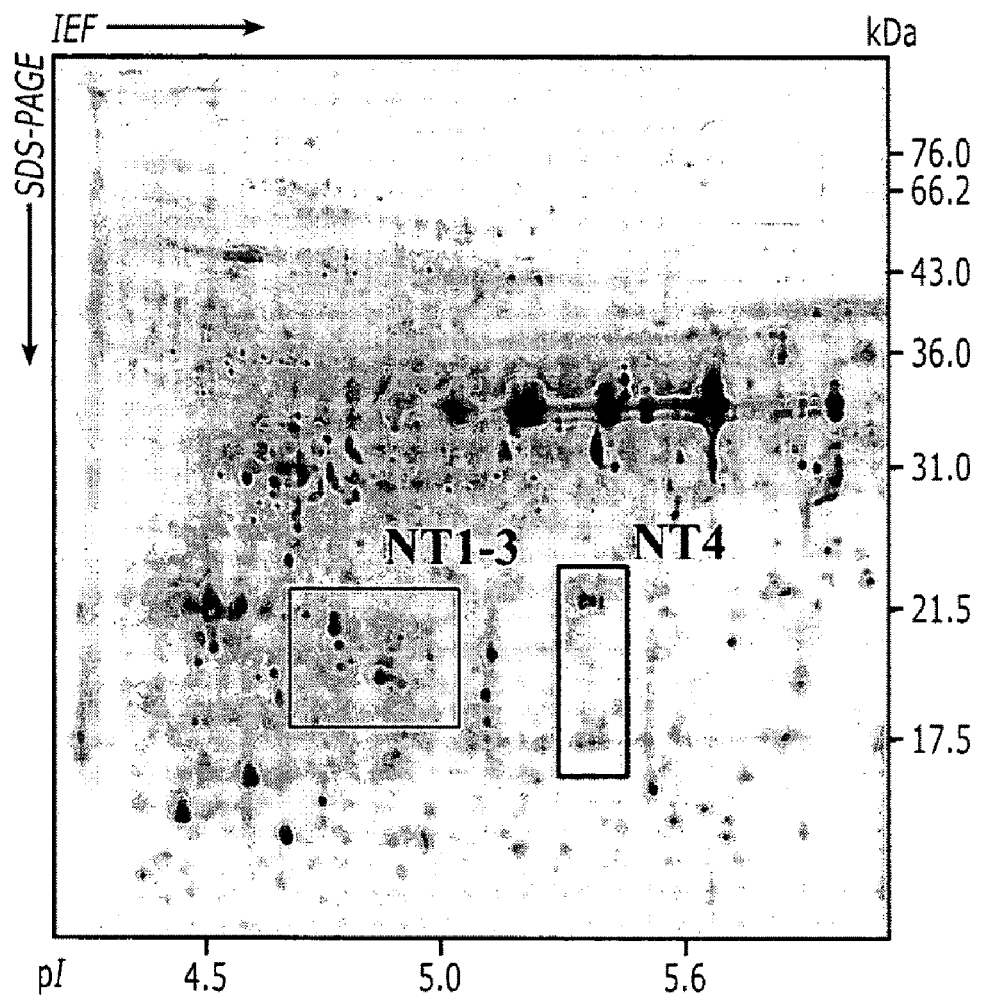
Figure 5F:
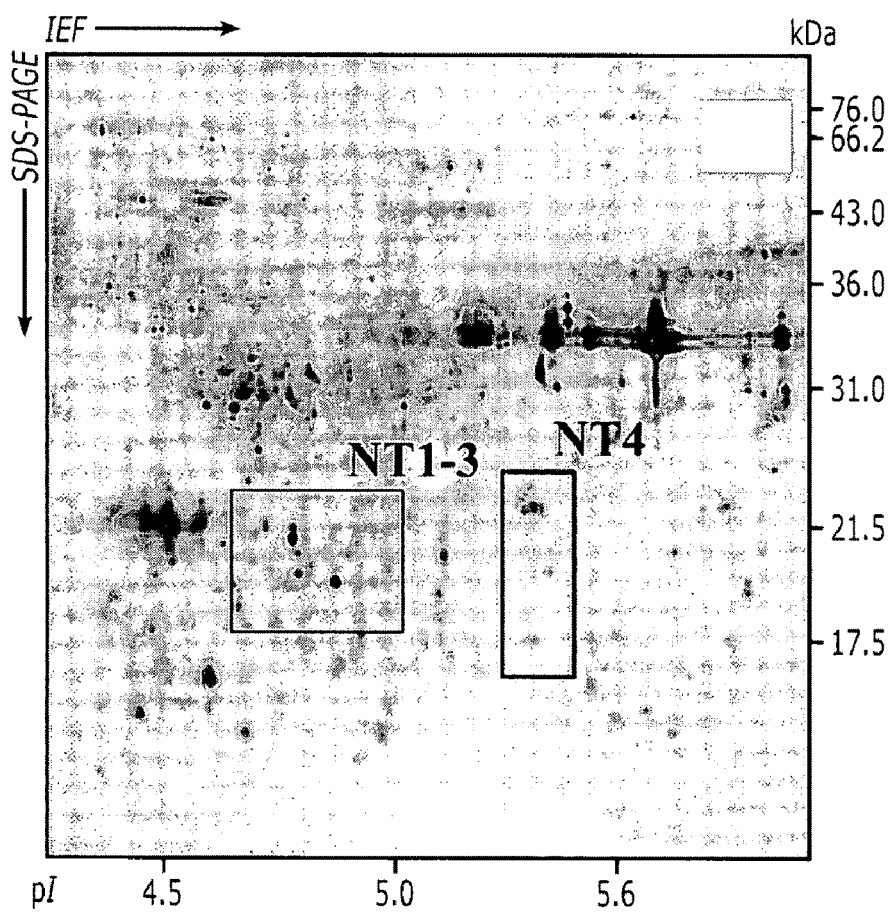
Figure 5G:
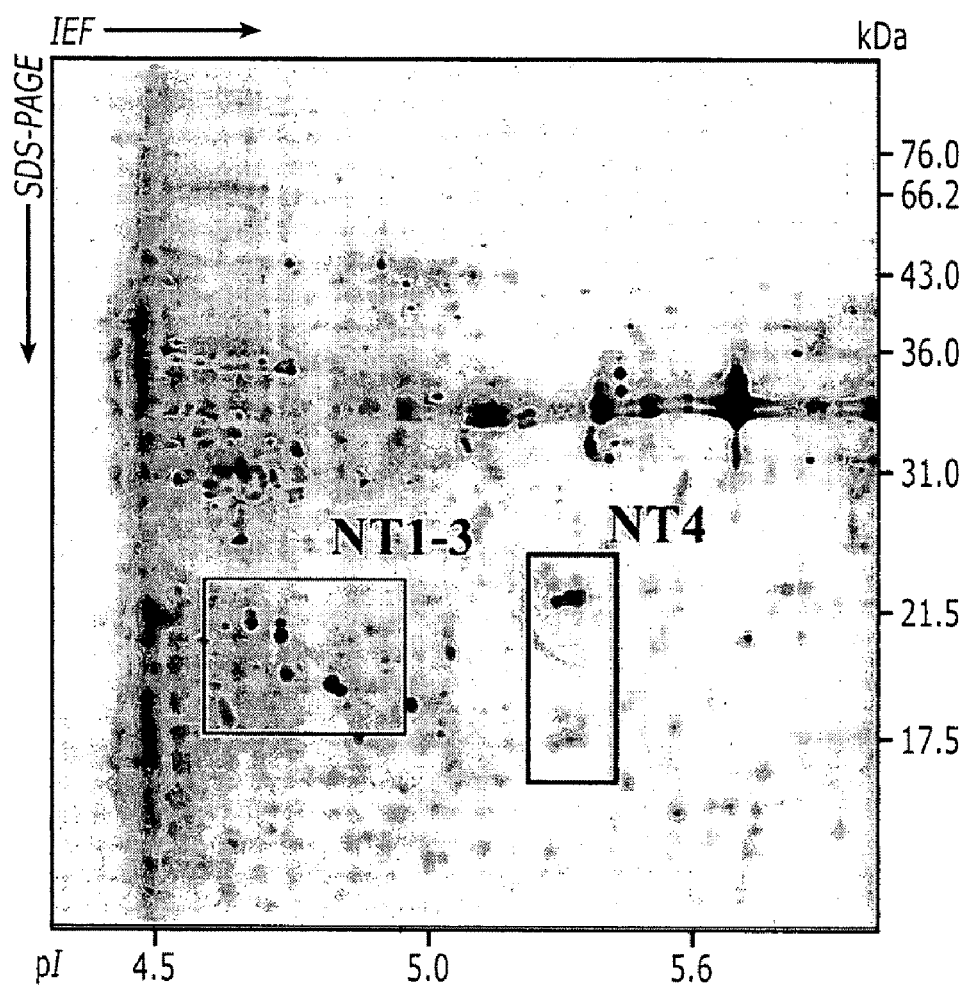
Figure 5H:
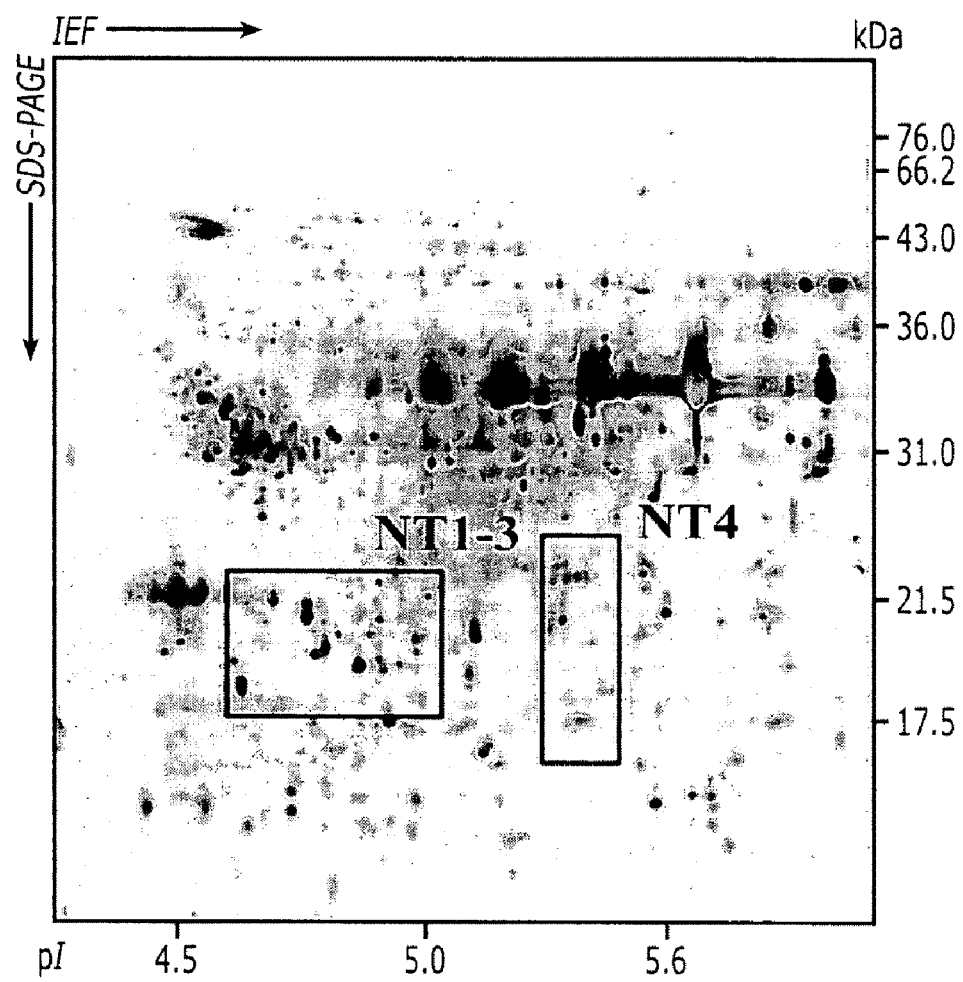
Figure 5I:
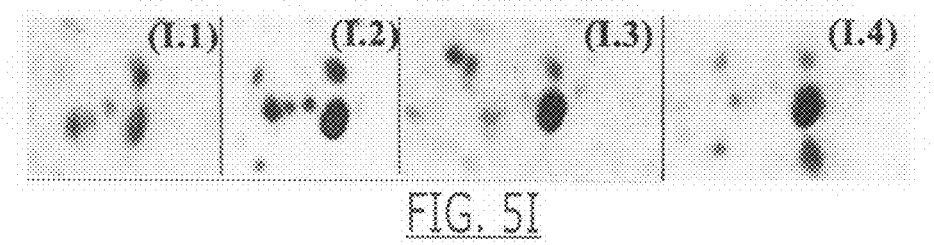
Figure 5J:
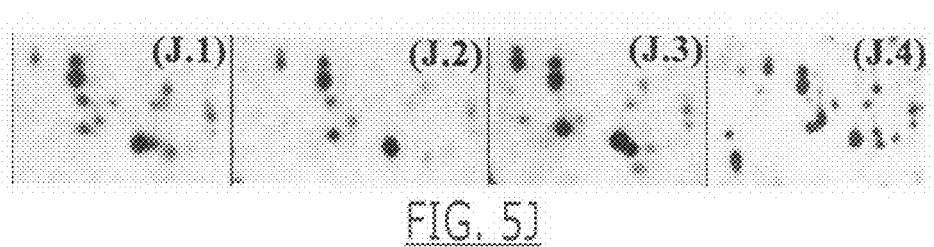

The possible effects of nutritional and environmental stresses and growth states on the expression of these strain-specific protein profiles were examined by analysis of the proteomic changes of two representative strains, the toxic strain AMKS2 and the non-toxic strain AMTK3 during a 5-day period as well as under light-, phosphorous-, and nitrogen-limited balance growth. Exponentially growing batch cultures of AMKS2 (toxic strain) and AMTK3 (non-toxic strain) of *A. minutum* were sampled for 5 days at circadian times separated by 12 h (i.e. 8 a.m. and 8 p.m. everyday) since *A. minutum* grew at the rate of 0.20 divisions d-1 in optimal environmental and nutritional conditions and completed the whole cell-cycle in approximately 3.5 days. The general protein patterns of the two strains were quite consistent with respect to different growth phases. Therefore, three representative gels were selected for each category and are shown in FIG. 4. For the toxic strain AMKS2, T1 showed a progressive increase in abundance from Day 1 to Day 5 (FIG. 4G), while T2 remained relatively constant over the entire growth cycle (FIGS. 4A to 4C). This protein increased from approximately 1.42% of the total quantified protein in Day 1 to 2.96% and 3.95% of the total quantified proteins in Day 3 and Day 5 respectively. For the non-toxic strain AMTK3, NT1, NT2 and NT3 increased in abundance between Day 1 and Day 3, but showed no further change in Day 5 (FIGS. 4D to 4F and 4H), while NT4 was predominant in all phases (FIGS. 4D to 4F).

The differentially expressed proteins in the two representative strains, AMKS2 and AMTK3, varied slightly under different environmental stresses and no major pattern differences could be detected (FIG. 5). However, the expression of T1 was much more abundant in light-starved (5B and I.2) and phosphate limited (5C and I.3) balanced growth cultures than nitrate limited balanced growth cultures (5A and I.1). T1 expression increased significantly in light starved and in P-limited balanced growth cultures relative to the N-limited balanced growth culture. The expression level of T1 decreased slightly (20%) in the N-limited balanced growth culture in comparison to the control culture. In contrast, the expression of NT1, NT2 and NT3 in the non-toxic strain of *A. minutum* remained constant under various stress condition (FIGS. 5E to 5G); the nutritional and environmental stresses had no apparent effect on their expressions (FIG. 5H). Expression of NT1, NT2 and NT3 appears to be completely independent of stress.

In some toxic algal cultures, bacteria living outside or inside the algal cells are either directly or indirectly associated with phytotoxin production [27]. Therefore extracts prepared from axenic and non-axenic cultures of *A. minutum* were compared in term of their toxicity and differential protein expression patterns. No significant differences were detected either in the toxin compositions (Table 1) or differential protein expression patterns among the axenic (FIGS. 5D and 5H) and non-anxenic cultures (FIG. 4).

Discussion

In nutrient replete cultures with no environmental stresses, toxin content peaked during the exponential growth phase. Dramatic increases and declines in toxin production were observed in P-limited and N-limited cultures respectively. Enhancement in toxicity was also observed in light-starved cultures. Our results were in agreement with previous findings on Alexandrium spp. by Anderson et al [31].

Despite the fact that no major protein expression pattern differences could be detected among algae in different growth phases and under different stresses, the relative abundance of protein, T1, of toxic strains of *A. minutum* showed important fluctuation throughout the different growth phases and under different stresses. Under constant growth conditions, levels of T1 were also found to vary in accordance with the growth cycle (FIG. 4A to 4C) and in direct proportion to the amount of toxin produced in the cells (Table 1). Anderson et al [32] suggested that cells produced toxins at rates approximating those needed to maintain a certain amount of toxin in the daughter cells after each cell division. Further investigation under different nutritional and environmental stresses revealed that T1 was up-regulated with phosphate- and light-limitation but down-regulated under nitrogen limitation. Toxin production appeared to be nitrogen regulated and this is again in agreement with one popular speculation that toxins might be a nitrogen storage product (approx. 33% of PST toxin weight is NH4+)[32] and their synthesis requires the availability of a source of nitrogen [33]. During nitrogen limitation, saxitoxin synthesis must compete for scarce nitrogen atoms with other essential N-containing compounds. Low toxin production rates and toxin contents under N limitation presumably result from competition for that element between saxitoxin and T1. Environmental enhancement in toxicity and expression of T1 were observed under light-starved and P-limited cultures. General synthesis of major cellular components required for cell division, such as phospholipids needed to make up novel cell membranes, and completion of DNA replication both required the presence of phosphorous. Under sub-optimal light conditions and severe P-limitation, cell division ceased and protein synthesis was reduced. Lack of competition for intracellular free amino acid from metabolic pathways specific to cell division and general protein synthesis resulted in increased concentration of necessary precursors and enzymes for rapid toxin synthesis. Therefore PST synthesis is promoted by phosphorous and light stresses but depressed by nitrogen deficiency, coinciding with the expression pattern of T1. A combination of the observations of algae response patterns during different physiological conditions and growth phases indicates that T1 expression is significantly related to toxin production.

The expression of NT1, NT2 and NT3 of a non-toxic strain of *A. minutum* increased from Day 1 to Day 5 (FIGS. 4D to 4E) and then remained constant most of the time (FIG. 4E to 4F). Nutritional and environmental stresses had no apparent effect on the expression of these proteins (FIGS. 5E to G) as their expression is observed to be completely independent of applied stressor conditions. They do not feature prominently in algal protein expression profiles at any time in the growth cycle of non-toxic algae. Despite the consistency of their expression, there may be environmental factors that act to limit the production of these proteins to only certain phases of the daily cycle. Since no difference in the amino acid sequence of NT1, NT2 and NT3 were found, they conclude that they are most likely subunits or breakdown products of the same protein complex.

The protein expression of NT4 of the non-toxic strain and T2 of the toxic strain of *A. minutum* remained fairly constant under all growth phases and growth conditions. From these results, we conclude that the expression of these differentially expressed proteins is a stable and steady metabolic activity and not a transient characteristic during the growth stages. They are not influenced by the physiological state or growth phases of the test alga under optimal conditions. Therefore, they are useful as taxonomic biomarkers to differentiate toxic and non-toxic strains grown in optimal environmental and nutritional conditions. Furthermore, the differentially expressed protein, T1, found in toxic strains, is of particular interest with respect to its potential use as taxonomic biomarker to differentiate toxic strains from non-toxic strains within the same species or as a toxin biomarker to study the PST biosynthetic pathway and detect the presence of toxin in biological samples.

The association of bacteria with dinoflagellates has been studied because of the possible role of bacteria in toxin synthesis. A number of dinoflagellates undergo sexual reproduction, passing through various life-cycle stages in addition to the vegetative form. The presence of bacteria within dinoflagellates has been well established [34], but their interaction with toxin biosynthesis still remains unknown. The toxin composition (Table 1) and differential protein expression profiles obtained from the axenic cultures of *A. minutum* (FIGS. 5D and 5H) revealed no significant difference with their non-axenic counterparts (FIGS. 4A and 4D). These findings rule out bacterial involvement in toxin synthesis in this test alga. Evidence from others indicated [32] that toxins may be synthesized using nitrogen that is recycled within the cells, rather than solely using inorganic nitrogen recently taken into the cells. This suggests that bacteria co-existing inside *A. minutum* might represent a "self-sustaining" source of organic nutrition to the algae in a mutualistic fashion.

The close association of T1 protein expression in toxic strains of *A. minutum* presents additional avenues for study of the metabolism of toxins in algae. The T1 protein may prove to be a pre-cursor or necessary catalyst for the production of toxin, which would provide an approach for inhibiting the production of toxin via down-regulation of the expression of the T1 protein.

Example 3

Figure 6A:
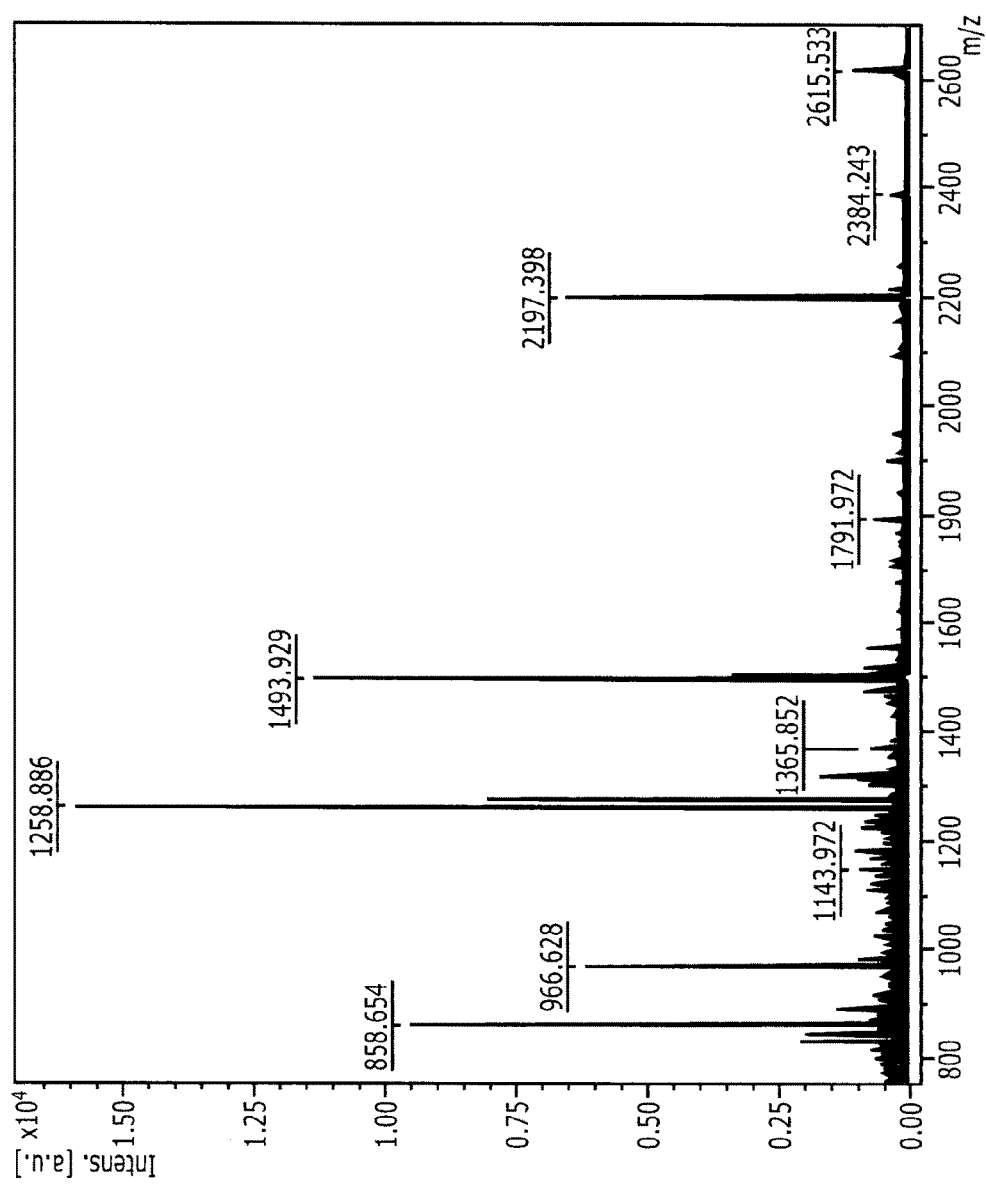

Protein Identification by MALDI-TOF Mass Spectrometry and N-terminal Amino Acid Sequencing By Edman Degradation Tryptic digestion of 2-DE gel spots corresponding to NT1, NT2, NT3 and T1 produced several peaks, all of which were common to all spots except for three peaks. Two peaks, 1258.9 Da and 2197.39 Da, were produced by digestion of the T1 spot and one peak at around 2223.1 Da was produced by from the NT1, NT2 and NT3 spots (FIG. 6). Amino acid sequencing found that these proteins have minor difference in their N-terminal amino acid sequence (Table 2) and these proteins may be isoforms of the same protein complex. The present invention includes methods, reagents and kits for determining whether a strain of algae is toxic in which an algal sample is assessed to determine which of these minor differences are present in the polypeptides in the sample or which of these minor differences are present in the polypeptides encoded by nucleic acids in the sample. For example, the methods, reagents or kits may utilize or contain antibodies or nucleic acid probes or primers which are capable of determining which of these minor differences are present in a polypeptide in the sample or which of these minor differences are encoded by a nucleic acid present in the sample.

TABLE 2

N-terminal sequencing of proteins NT1, NT2 and NT3 from nontoxic strain, AMTK-3 and T1 from toxic strain. AMKS-2 of *Alexandrium minutum*.

| Protein spots | N-terminal amino acid sequences | Matching proteins in the protein database |
|---|---|---|
| NT1 | SAEYL ERLGP KDADV PFTAA AGGGE EPVVF DDRP (SEQ ID NO: 3) | |
| NT2 | SAEYL ERLGP KDADV PFTAA PGGPE HPVTF DKRP (SEQ ID NO: 4) | |
| NT3 | SAEYL ERLGP KDADV PFTAA PGGPE HSVTF FKRP (SEQ ID NO: 5) | |
| T1 | SAEYL ERLGP KDADV PFTAA PGGAE HPVTF K (SEQ ID NO: 6) | |

Discussion

Figure 6B:
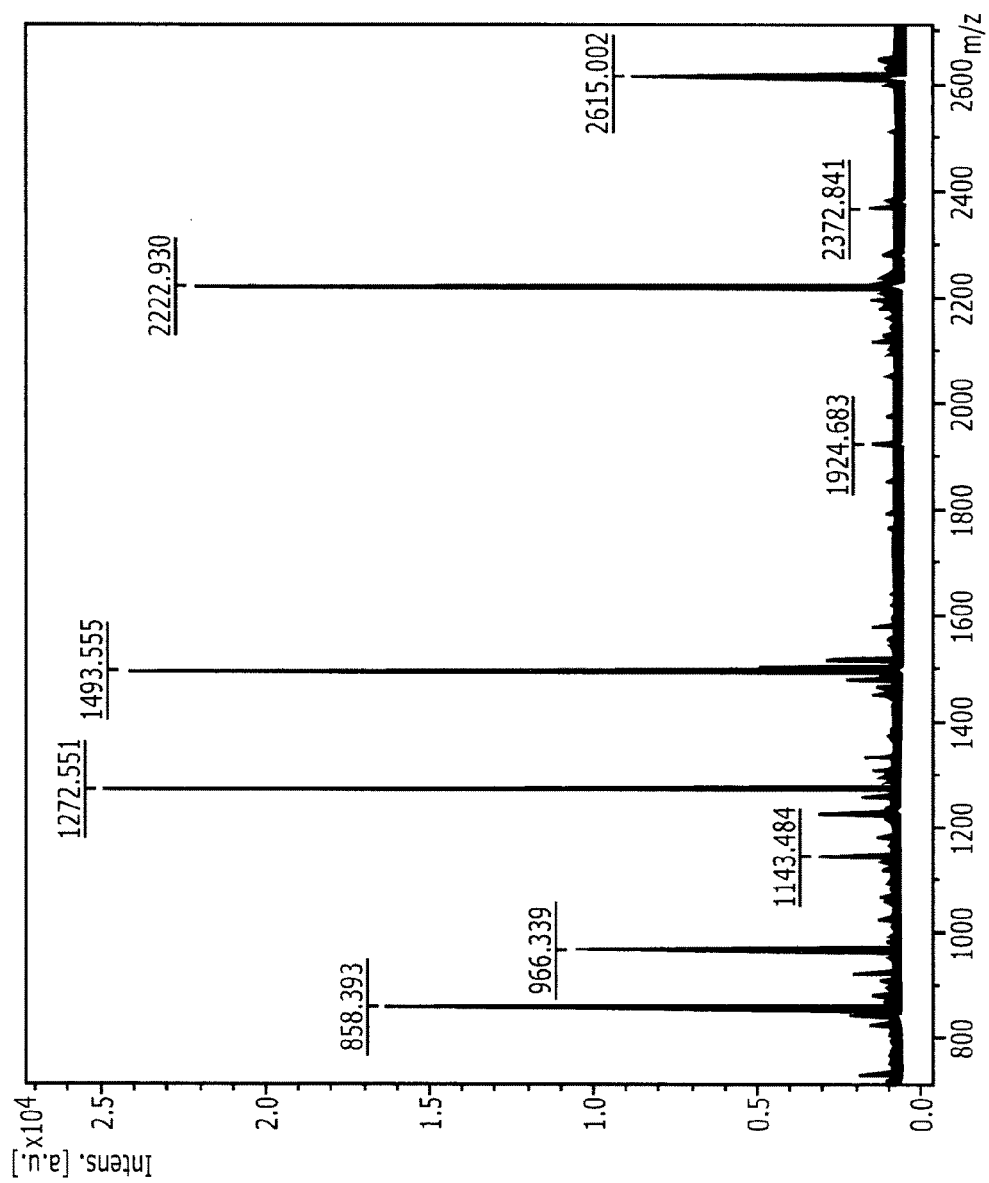
Figure 6C:
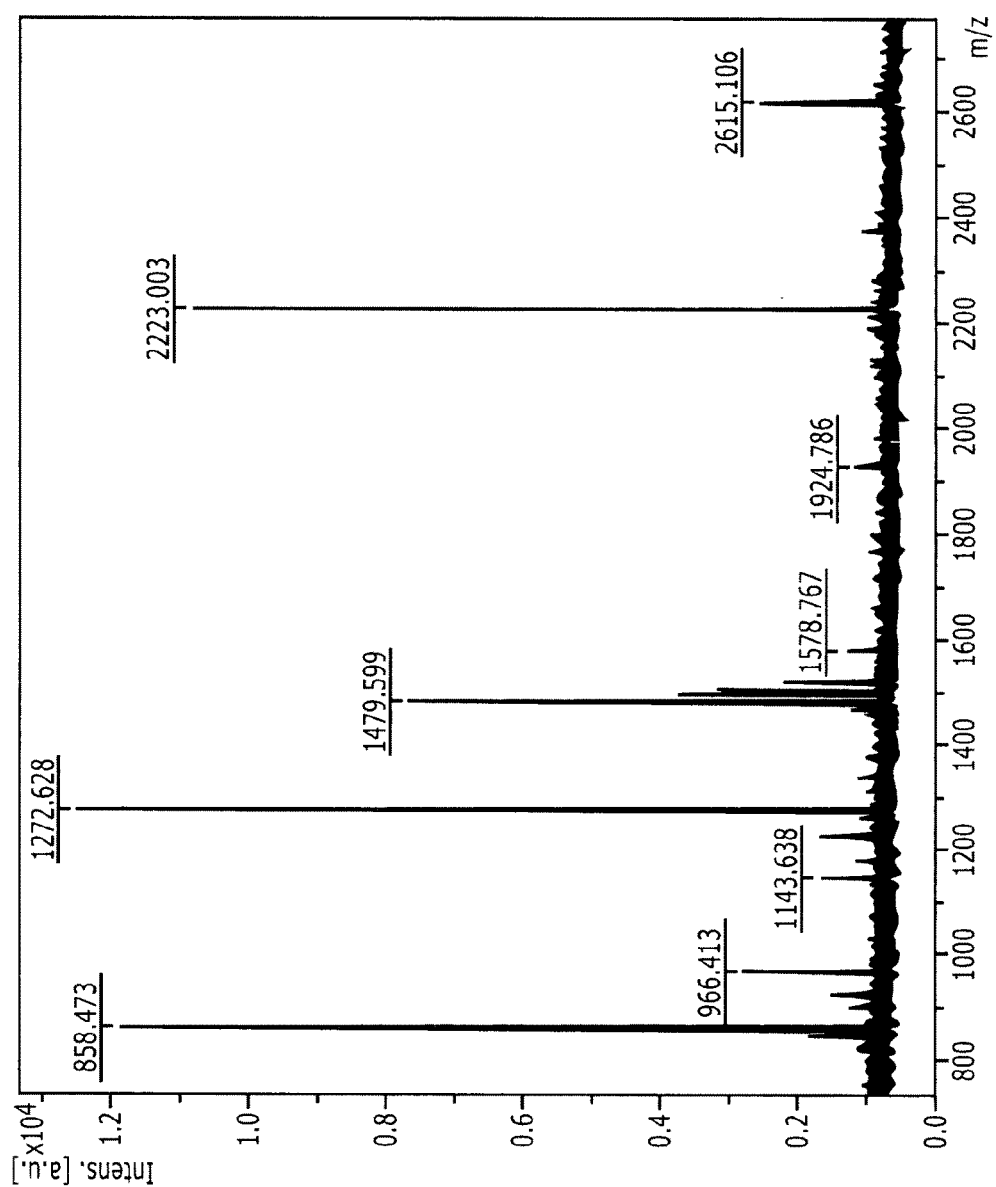

In the present study, four proteins which have the potential to serve as taxonomic biomarkers were further characterized by a combination of MALDI-TOF mass spectrometry and N-terminal amino acid sequencing by Edman degradation. Results revealed that NT1, NT2 and NT3 share similar peptide mass fingerprints (PMFs), indicating that these spots are isoforms of the same proteins or closely-related proteins (FIGS. 6B to 6C). Despite the fact that mass spectrum of peptide tryptic digest of T1 (FIG. 6A) illustrated a different set of peptide mass fragments when compared to NT1, NT2 and NT3, the N-terminal sequences of these spots indicate that they are isoforms of the same protein (Table 1). Increases or decreases in peptide mass and alterations of pI values can be due to post-translational processing. The process of how these electrophoretically distinct isoforms, which are characteristic of different strains, were modified in toxic and nontoxic strains is a subject of ongoing interest.

Since there is little genomic sequence data currently available for dinoflagellates, we compared proteome analysis with methods using N-terminal Edman sequencing to analysis using MALDI-TOF MS analysis of tryptic digests based on 2D-PAGE to differentiate toxic and nontoxic strains of *A. minutum*. Protein identification by PMF was overall more successful than N-terminal sequencing for these two categories, since small changes in sequence can change the endoprotease and exoprotease cleavage sites [35] and a different set of peptide mass fragments will be obtained despite the proteins all having similar or identical partial amino acid sequences. The unique peptide mass fragments found in toxic and nontoxic strains can be used to elucidate the functionally significant structural modifications in these proteins which might help to gain an understanding of the biochemical pathways operating in the dinoflagellates and the biosynthetic mechanism of the secondary metabolites.

Example 4

Isolation and Characterization of Full-length Biomarker Genetic Coding Sequences Through the use of 2-DE gel electrophoresis, differential protein expression analysis and N-terminal peptide sequencing, partial N-terminal sequences have been obtained for NT1, NT2, NT3, NT4 and T1.

Based on the N-terminal sequences obtained, degenerate oligonucleotides for reverse-transcription-polymerase chain reaction (RT-PCR) amplification are designed and synthesized. Total RNA is isolated from cultures of toxic and non-toxic *A. minutum* strains and reverse transcribed using oligo (dT). After first strand synthesis of DNA from the total RNA samples is completed, PCR with degenerate oligonucleotides is used to generate partial cDNAs for the biomarker proteins. The cDNA fragments are treated enzymatically to create blunt-ended fragments, then they are ligated to a bacterial propagation vector such as pUC8. Individual plasmid clones are sequenced to identify those with N-terminal sequences matching the partial N-terminal sequence previously determined for the biomarker proteins.

Plasmids containing putative partial cDNAs of the biomarker proteins are used with established laboratory techniques known to persons with skill in the art for isolation of the remaining coding sequence(s) for the biomarker proteins. In one approach, total RNA from algae samples are used with commercially available kits to create genomic libraries for the algal strains. Briefly, total RNA is reverse transcribed and cloned into commercially available vectors which permit the insertion of cloned cDNAs into a lambda bacteriophage library. The library is plated with host bacteria and hybridization membranes are placed onto the plates and spatially marked. The hybridization membranes are lifted from the plates and treated to expose the library DNA. Partial cDNA sequences of biomarker genetic sequence are used to create labeled probe cDNAs and the labeled probes are hybridized to the library hybridization membranes. Exposure to film reveals the locations on the hybridization members where probe cDNA have hybridized with lambda phage library genetic material. Phage samples from the plates are isolated and replated at a lower density. Probe hybridization followed by replating of isolated phage at a lower density is repeated until positive singular isolated phage samples can be extracted from the plate. The library sequences in these phage samples are then sequenced. Analysis of the genetic sequences contained within the phage library samples will reveal whether the entire coding sequence(s) of the biomarker proteins, extending into untranslated 3' cDNA sequence, have been obtained. If not, further rounds of lambda library screenings can be performed, using lambda library sequences that are 3' to the sequence of the original probe as probes for the additional rounds of screenings. Once lambda library sequences have been isolated that overlap an entire coding sequence for a biomarker protein, the sequence can be assembled into a single expression vector containing a single contiguous coding sequence for the protein.

Example 4A

3' rapid amplification of cDNA ends (3' RACE) cloning was performed according to methods previously described (Frohman M A, Dush M K, Martin G R. Rapid production of full-length cDNAs from rare transcripts: amplification using a single gene-specific oligonucleotide primer. *Proc Natl Acad Sci USA*. 1988, 85:8998-9002; Ohara O, Dorit R L, Gilbert W. One-sided polymerase chain reaction: the amplification of cDNA. *Proc Natl Acad Sci USA*. 1989, 86:5673-7) to obtain partial DNA sequence of T1. Briefly, total RNA was extracted from the dinoflagellate using Trizol reagent. cDNA was then synthesized by using the 3'-RACE-oligo-dT primer with the following sequence:

(SEQ ID NO: 7)
5'-GGC CAC GCG TCG ACT AGT ACT TTT TTT TTT TTT TTT T-3'

3'-RACE was then performed by PCR using the gene specific primer 1 (5'-CCC AAA GAC GCG GAC GTG CC-3') (SEQ ID NO: 8) and the universal primer (5'-GGC CAC GCG TCG ACT AGT AC-3') (SEQ ID NO: 9), and the cDNA as template. The PCR condition used was: initial denaturation at 95° C. for 3 minutes, followed by denaturation at 94° C. for 40 seconds, annealing at 60° C. for 40 seconds and extension at 72° C. for 40 seconds, for 35 cycles. The resulting PCR product was diluted 100-fold and used as template in the second round of PCR. Gene specific primer 2 (5'-GCG GAC GTG CCC TTC ACG GC-3') (SEQ ID NO: 10) and universal primer (5'-GGC CAC GCG TCG ACT AGT AC-3') (SEQ ID NO: 9) was used in the second round of PCR. Conditions of the second round of PCR was initial denatured at 95° C. for 3 minutes, followed by denaturation at 94° C. for, 40 seconds, annealing at 60° C. for 40 seconds and extension at 72° C. for 40 seconds, for 35 cycles. PCR product obtained was cloned and sequenced.

With the 3' rapid-amplification-of-cDNA-ends (3' RACE) cloning method as described above, part of the DNA sequence coding for T1 was found to be:

(SEQ ID NO: 2)
AGTGCCGAGTACCTAGAACGACTAGGGCCCAAAGACGCG

GACGTGCCCTTCACGGCCGCCCCTGGCGGCGCTGAGCACCCGGTGACCTT

CAAGAAGCGGCCCTTCGGCATCTTGCGCTACCAGCCGGGCGCGGGCATGA

AGGGTGCCATGGTGATGGAGATCATTCCCAAGTCGCGCTACCCCGGCGAC

CCCCAGGGCCAGGCGTTCTCCTCGGGCGTGCAGAGCGGATGGGTCGTCAA

GTCGATCAACGGTGAGGACGTGCTGACGGCGGACTTCGGCCGCATCATGG

ACTTGCTGGACGACGAGGTGGCCGACCCGCGCTTCTCCAAGTCGACGGCC

TTGGCCCTCGAGAAGCAGGGCGGCCGCTTGGCAGCGCCGGTGGAGGCGCC

CCTCGGGGTCGTCTTCGCGGAGATCCCGGGCTACCAGGGCAACTTCGCGA

CGCTCAGCCAGGACGGCCAGGACGGCTTCGCGCGTTA.

The above example represents one possible approach to obtaining the full coding sequence for a gene when only a small portion of 5' end sequence has been obtained. Additional approaches for reaching the same goal are known to those with skill in the art.

Example 5

Production of Monoclonal Antibodies to Taxonomic and Toxic Biomarker Proteins The previous example outlined a process for obtaining a full-length coding sequence for a biomarker protein of the invention. Having obtained this coding sequence, monoclonal antibodies are produced using the sequence with skills and protocols known to those with skill in the art. Monoclonal antibodies to biomarker proteins provide a powerful research and diagnostic tool for exploring the metabolism and synthesis of algal toxins and detecting the presence of algal toxins in biological samples. A procedure that can be used to produce monoclonal antibodies from the genetic sequence(s) isolated in the previous example is outlined below. However, there are multiple systems and protocols to accomplish this goal and this example is not intended to limit the methods of the invention to any one approach or system. The procedure outlined below described the production of monoclonal antibodies from one full-length coding sequence of an algal biomarker protein. The procedure may be used to synthesize monoclonal antibodies from other full-length coding sequences of algal biomarker proteins, should such sequences exist, as well as from partial cDNA sequences derived from genetic material that codes for an algal biomarker protein.

The coding sequence for an algal biomarker protein is cloned into a commercially available bacterial expression vector that will express the protein with a 6× histidine tag at either the C-terminal or N-terminal end of the biomarker protein. The vector is transformed into *E. Coli* and the tagged protein is expressed in the bacteria; the recombinant biomarker protein is then purified after extraction from the bacteria by virtue of commercially available $Ni^{2+}$ resin that binds the 6× histidine tag.

BALB/c mice are immunized with the purified, recombinant biomarker protein in Freund's complete adjuvant. The mice receive immunization boosts at two week intervals by injection of recombinant biomarker protein in Freund's incomplete adjuvant initially and with just the recombinant protein for a second and final injection. Splenocytes are collected two days after the final injection and fused with a myelonoma cell line. Screenings for hybridomas producing anti-biomarker murine Ab are performed using ELISA. To provide antigen for ELISA screenings, recombinant biomarker protein from *E. Coli* can be used, or alternatively a mammalian or insect cell expression system, utilizing mammalian expression vectors and COS cells or baculovirus vectors and Th5 cells, for example, can be used to produce biomarker antigen protein. Multiple methods of expressing large quantities of recombinant proteins are known to those with skill in the art. Hybridoma cultures that test positive for Ab to the algal biomarker protein are then replated at limiting dilutions and retested. Testing and replated are repeated until clonal hybridoma cultures producing monoclonal antibodies to the algal biomarker protein are produced. Clonal hybridoma cultures are then used to produce large quantities of monoclonal Ab to the algal biomarker protein via techniques known to those with skill in the art. These antibodies can then be used in basic algae research and in commercial screening applications for algal strains and toxins.

In some instances it may be desirable to produce antibodies which are capable of distinguishing between the toxicity associated T1 polypeptide comprising SEQ ID NO: 1 and proteins from non-toxic strains such as NT1, NT2 and NT3 (SEQ ID NOS: 3-5). Such antibodies can be obtained by generating monoclonal antibodies against one of the T1, NT1, NT2 or NT3 polypeptides and assessing the ability of these antibodies to bind to the other polypeptides to identify antibodies specific to either the T1, NT1, NT2, or NT3 polypeptides. For example, in one embodiment monoclonal antibodies may be generated against T1. The antibodies against T1 are then placed in contact with NT1, NT2 or NT3 and their ability to bind NT1, NT2 or NT3 is assessed. Those monoclonal antibodies which bind to T1 which bind with significantly lower affinity or do not bind at all to NT1, NT2 or NT3 may be used in kits for determining whether a strain of algae is toxic. If a sample comprising polypeptides from the strain being evaluated binds a T1 specific antibody which binds with significantly lower affinity or which does not bind at all to NT1, NT2 or NT3, then the strain is a toxic strain. Likewise, if a sample comprising polypeptides from the strain being evaluated binds to an antibody which binds NT1, NT2 or NT3 but which binds T1 with a significantly lower affinity or which does not bind T1 at all, then the strain being evaluated is non-toxic.

In some embodiments the antibody specifically binds to one of the following polypeptides:

(1) a portion of SEQ ID NO: 1 which includes the sequence AP;

(2) a portion of SEQ ID NO: 1 which includes the sequence PG;

(3) a portion of SEQ ID NO: 1 which includes the sequence GA;

(4) a portion of SEQ ID NO: 1 which includes the sequence AE;

(5) a portion of SEQ ID NO: 1 which includes the sequence EH;

(6) a portion of SEQ ID NO: 1 which comprises the sequence HP;

(7) a portion of SEQ ID NO: 1 which includes the sequence PV;

(8) a portion of SEQ ID NO: 1 which includes the sequence VT;

(9) a portion of SEQ ID NO: 1 which includes the sequence TF;

(10) a portion of SEQ ID NO: 1 which includes the sequence FK;

(11) a portion of SEQ ID NO: 1 which includes the sequence KK;

(12) a portion of SEQ ID NO: 1 which includes the sequence KR;
(13) a portion of SEQ ID NO: 3 which includes the sequence AAA;
(14) a portion of SEQ ID NO: 3 which includes the sequence AG;
(15) a portion of SEQ ID NO: 3 which includes the sequence GGG;
(16) a portion of SEQ ID NO: 3 which includes the sequence GE;
(17) a portion of SEQ ID NO: 3 which includes the sequence EE;
(18) a portion of SEQ ID NO: 3 which includes the sequence EP;
(19) a portion of SEQ ID NO: 3 which includes the sequence VV;
(20) a portion of SEQ ID NO: 3 which includes the sequence VF;
(21) a portion of SEQ ID NO: 3 which includes the sequence FD;
(22) a portion of SEQ ID NO: 3 which includes the sequence DD;
(23) a portion of SEQ ID NO: 4 which includes the sequence GGP;
(24) a portion of SEQ ID NO: 3 which includes the sequence PE;
(25) a portion of SEQ ID NO: 3 which includes the sequence FD;
(26) a portion of SEQ ID NO: 3 which includes the sequence DK;
(27) a portion of SEQ ID NO: 5 which includes the sequence GGP;
(28) a portion of SEQ ID NO: 5 which includes the sequence PE;
(29) a portion of SEQ ID NO: 5 which includes the sequence HS;
(30) a portion of SEQ ID NO: 5 which includes the sequence SV; and
(31) a portion of SEQ ID NO: 5 which includes the sequence FF.

Example 6

Screening and Identification of Proteins that Interact with a Peptide of the Invention In some embodiments of the invention, algal proteins involved in toxin metabolism and proteins that toxin metabolism proteins interact with can be studied. Some embodiments use the yeast two hybrid system or a variant of this system to find and identify peptides that interact with polypeptide sequences that comprise the peptide T1 (hereby known as "T1 polypeptide"). The yeast two-hybrid system is designed to study protein-protein interactions in vivo (Fields and Song, 1989), and relies upon the fusion of a bait protein to the DNA binding domain of the yeast Gal4 protein. This technique is also described in the U.S. Pat. No. 5,667,973 and the U.S. Pat. No. 5,283,173 (Fields et al.) the technical teachings of both patents being herein incorporated by reference.

The general procedure of library screening by the two-hybrid assay may be performed as described by Harper et al. (1993) or as described by Cho et al. (1998) or also Fromont-Racine et al. (1997).

The bait protein or polypeptide comprises, consists essentially of, or consists of an a polypeptide or a fragment comprising a contiguous span of at least 4 amino acids, preferably at least 6 amino acids, more preferably at least 8 to 10 amino acids, and more preferably at least 12, 15, 20, 25, 30, 40, 50, or 100 amino acids of a polypeptide that comprises T1.

More precisely, the nucleotide sequence encoding the polypeptide comprising the sequence T1 or a fragment or variant thereof is fused to a polynucleotide encoding the DNA binding domain of the GAL4 protein, the fused nucleotide sequence being inserted in a suitable expression vector, for example pAS2 or pM3.

Then, a cDNA library is constructed in a specially designed vector, such that the cDNA insert is fused to a nucleotide sequence in the vector that encodes the transcriptional domain of the GAL4 protein. The cDNA insert can come from a variety of sources. In some embodiments, the cDNA insert comprises sequence from a species of algae. In some embodiments, the cDNA insert comprises sequence from a human being. Preferably, the vector used is the pACT vector. The polypeptides encoded by the nucleotide inserts of the cDNA library are termed "prey" polypeptides.

A third vector contains a detectable marker gene, such as beta galactosidase gene or CAT gene that is placed under the control of a regulation sequence that is responsive to the binding of a complete Gal4 protein containing both the transcriptional activation domain and the DNA binding domain. For example, the vector pG5EC may be used.

Two different yeast strains are also used. As an illustrative but non limiting example the two different yeast strains may be the following:

Y190, the phenotype of which is (MATa, Leu2-3, 112 ura3-12, trp1-901, his3-D200, ade2-101, gal4Dgal180D URA3 GAL-LacZ, LYS GAL HIS3, cyh$^r$);

Y187, the phenotype of which is (MATa gal4 gal80 his3 trp1-901 ade2-101 ura3-52 leu2-3, -112 URA3 GAL-lac-Zmet$^-$), which is the opposite mating type of Y190.

Briefly, 20 μg of pAS2/T1-polypeptide and 20 μg of pACT-cDNA library are co-transformed into yeast strain Y190. The transformants are selected for growth on minimal media lacking histidine, leucine and tryptophan, but containing the histidine synthesis inhibitor 3-AT (50 mM). Positive colonies are screened for beta galactosidase by filter lift assay. The double positive colonies (His$^+$, beta-gal$^+$) are then grown on plates lacking histidine, leucine, but containing tryptophan and cycloheximide (10 mg/ml) to select for loss of the pAS2/T1-polypeptide plasmid but retention of pACT-cDNA library plasmids. The resulting Y190 strains are mated with Y187 strains expressing the T1 polypeptide or non-related control proteins; such as cyclophilin B, lamin, or SNF1, as Gal4 fusions as described by Harper et al. (1993) and by Bram et al. (Bram R J et al., 1993), and screened for beta galactosidase by filter lift assay. Yeast clones that are beta gal—after mating with the control Gal4 fusions are considered false positives.

In another embodiment of the two-hybrid method according to the invention, interaction between polypeptide sequences that comprise the peptide T1 (T1 polypeptide) or a fragment or variant thereof with algal or cellular proteins may be assessed using the Matchmaker Two Hybrid System 2 (Catalog No. K1604-1, Clontech). As described in the manual accompanying the Matchmaker Two Hybrid System 2 (Catalog No. K1604-1, Clontech), the disclosure of which is incorporated herein by reference, nucleic acids encoding polypeptide sequences that comprise the peptide T1 or a portion thereof, are inserted into an expression vector such that they are in frame with DNA encoding the DNA binding domain of the yeast transcriptional activator GAL4. A desired cDNA, preferably algal cDNA, is inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells which are positive for both the histidine selection and the lacZ assay contain sequences that permit, facilitate, or lead to interaction between a polypeptide sequence that comprises the peptide T1 and the protein or peptide encoded by the initially selected cDNA insert; including the interacting sequences themselves. Cultures of these yeast cells are grown in quantity and the library plasmid containing the interacting sequence is isolated. The library plasmid's cDNA insert is sequenced to reveal the identity of the interacting protein (if known and published). Alternatively, the sequence information from the cDNA insert can be used to produce reagents for finding the rest of the sequence of the polypeptide for which the cDNA insert codes a portion of the amino acid sequence.

Example 7

Screening for and Identifying Compounds that Interact with Peptides of the Invention Additional embodiments of the invention provide means to screen and identify compounds that can bind or otherwise interact with a protein or peptide of the invention.

The test compounds which may be used in any of the assays described herein can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is used with peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc Natl Acad Sci USA 89:1865-1869) or on phage (Scott and Smith (1990) Science 249:386-390); (Devin (1990) Science 249:404-406); (Cwirla et al. (1990) Proc. Natl. Acad. Sci. 87:6378-6382); (Felici (1991) J. Mol. Biol. 222:301-310); (Ladner supra.).

Determining the ability of the test compound to inhibit or increase the activity of a polypeptide comprising the sequence T1 can be accomplished, for example, by coupling the polypeptide or a biologically active portion thereof with a radioisotope or enzymatic label such that binding of the polypeptide or biologically active portion thereof to its cognate target molecule can be determined by detecting the labeled polypeptide or biologically active portion thereof in a complex. For example, compounds (e.g., a polypeptide comprising the sequence T1 or biologically active portion thereof) can be labeled with 125 I, 35 S, 14 C, or 3 H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product. The labeled molecule is placed in contact with its cognate molecule and the extent of complex formation is measured. For example, the extent of complex formation may be measured by immuno precipitating the complex or by performing gel electrophoresis. The extent of complex formation in the presence and absence of the test compound is compared.

It is also within the scope of this invention to determine the ability of a compound (e.g., a polypeptide comprising the sequence T1 or biologically active portion thereof) to interact with its cognate target molecule without the labeling of any of the interactants. Interaction of the polypeptide comprising the sequence T1 or biologically active fragment thereof with the target molecule may be measured in the presence or absence of the test compound to identify compounds which increase or decrease the extent of interaction. For example, a microphysiometer can be used to detect the interaction of a compound with its cognate target molecule without the labeling of either the compound or the target molecule. McConnell, H. M. et al. (1992) Science 257:1906-1912. A microphysiometer such as a cytosensor is an analytical instrument that measures the rate at which a cell acidifies its environment using a light-addressable potentiometric sensor (LAPS). Changes in this acidification rate can be used as an indicator of the interaction between compound and receptor.

In more than one embodiment of the above assay methods of the present invention, it may be desirable to immobilize a polypeptide comprising the sequence T1 or its target molecule to facilitate separation of complexed from uncomplexed forms of one or both of the proteins, as well as to accommodate automation of the assay. Binding of a test compound to a polypeptide comprising the sequence T1, or interaction of the polypeptide with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/T1-comprising polypeptide fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or the a polypeptide comprising the sequence T1, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of the T1-comprising polypeptide's binding or activity determined using standard techniques.

Other techniques for immobilizing proteins on matrices can also be used in the screening assays of the invention. For example, either a T1-comprising polypeptide or a T1-comprising polypeptide target molecule can be immobilized utilizing conjugation of biotin and streptavidin. Biotinylated T1-comprising polypeptides or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with a T1-comprising polypeptide or target molecules but which do not interfere with binding of the T1-comprising polypeptide to its target molecule can be derivatized to the wells of the plate, and unbound target or T1-comprising polypeptide would be trapped in the wells by antibody conjugation. Methods for detecting such complexes, in addition to those described above for the GST-immobilized complexes, include immunodetection of complexes using antibodies reactive with a T1-comprising polypeptide or target molecule, as well as enzyme-linked assays which rely on detecting an enzymatic activity associated with a T1-comprising polypeptide or target molecule.

It would be apparent to one with skill in the art that there are multiple other ways to use the peptides of the invention to screen for compound that interact with the peptides of the invention. The above example is not intended to limit the use of the peptides of the invention to any of the described systems.

Example 8

Nucleic Acid Based Methods for Determining Whether a Strain of Algae is Toxic

In some embodiments of the present invention, a nucleic acid sample is obtained from a strain of algae to be evaluated for toxicity. The nucleic acid sample is contacted with a nucleic acid probe or primer which is capable of distinguishing between nucleic acids encoding the toxicity associated polypeptide of SEQ ID NO: 1 and nucleic acids which do not encode a toxicity associated polypeptide. For example, the nucleic acid which does not encode a toxicity associated polypeptide may be a nucleic acid which encodes the NT1, NT2 or NT3 polypeptide. Thus, a primer or probe specific to nucleic acid which encodes the T1 polypeptide may be placed in contact with the sample, a hybridization reaction or amplification reaction is performed, and the presence or absence of hybridization or amplification is assessed. Hybridization or amplification indicates that the strain comprises a nucleic acid encoding the T1 polypeptide, thereby indicating that the strain is toxic. Likewise, a primer or probe specific to a nucleic acid encoding NT1, NT2, or NT3 may be placed in contact with the sample. Hybridization or amplification indicates that the strain encodes NT1, NT2 or NT3, thereby indicating that the strain is not toxic.

The nucleic acid primer may be an allele specific primer which is used in an allele specific amplification procedure. Numerous methods for conducting allele specific amplification are familiar to those skilled in the art, including the methods set forth in U.S. Pat. No. 6,638,719, 6,083,698 and 5,639,611, the disclosures of which are incorporated herein by reference in their entireties. Nucleic acid primers specific for nucleic acids encoding T1 or specific for nucleic acids encoding NT1, NT2 or NT3 may be used in such allele specific amplification procedures.

Alternatively, probes which specifically hybridize to nucleic acids encoding T1, NT1, NT2 or NT3 may be used in a Southern blot or Northern blot procedure. Hybridization may be conducted under conditions in which a T1 specific probe will specifically hybridize to a nucleic acid encoding T1 but will not hybridize or will hybridize to a significantly lesser degree to a nucleic acid encoding NT1, NT2 or NT3. Alternatively, hybridization may be conducted under conditions in which a NT1, NT2 or NT3 specific probe will specifically hybridize to a nucleic acid encoding NT1, NT2 or NT3 but will not hybridize or will hybridize to a significantly lesser degree to a nucleic acid encoding T1. If a nucleic acid probe specific for T1 hybridizes to a nucleic acid sample from a strain of algae being evaluated, the strain is toxic. Alternatively, if a nucleic acid probe specific for a nucleic acid encoding NT1, NT2 or NT3 hybridizes to the sample then the strain of algae being evaluated is non-toxic.

In some embodiments, the primer or probe specifically amplifies or specifically hybridizes to a nucleic acid comprising a sequence encoding one of the following polypeptides:

(1) a portion of SEQ ID NO: 1 which includes the sequence AP;

(2) a portion of SEQ ID NO: 1 which includes the sequence PG;

(3) a portion of SEQ ID NO: 1 which includes the sequence GA;

(4) a portion of SEQ ID NO: 1 which includes the sequence AE;

(5) a portion of SEQ ID NO: 1 which includes the sequence EH;

(6) a portion of SEQ ID NO: 1 which comprises the sequence HP;

(7) a portion of SEQ ID NO: 1 which includes the sequence PV;

(8) a portion of SEQ ID NO: 1 which includes the sequence VT;

(9) a portion of SEQ ID NO: 1 which includes the sequence TF;

(10) a portion of SEQ ID NO: 1 which includes the sequence FK;

(11) a portion of SEQ ID NO: 1 which includes the sequence KK;

(12) a portion of SEQ ID NO: 1 which includes the sequence KR;

(13) a portion of SEQ ID NO: 3 which includes the sequence AAA;

(14) a portion of SEQ ID NO: 3 which includes the sequence AG;

(15) a portion of SEQ ID NO: 3 which includes the sequence GGG;

(16) a portion of SEQ ID NO: 3 which includes the sequence GE;

(17) a portion of SEQ ID NO: 3 which includes the sequence EE;

(18) a portion of SEQ ID NO: 3 which includes the sequence EP;

(19) a portion of SEQ ID NO: 3 which includes the sequence VV;

(20) a portion of SEQ ID NO: 3 which includes the sequence VF;

(21) a portion of SEQ ID NO: 3 which includes the sequence FD;

(22) a portion of SEQ ID NO: 3 which includes the sequence DD;

(23) a portion of SEQ ID NO: 4 which includes the sequence GGP;

(24) a portion of SEQ ID NO: 3 which includes the sequence PE;

(25) a portion of SEQ ID NO: 3 which includes the sequence FD;

(26) a portion of SEQ ID NO: 3 which includes the sequence DK;

(27) a portion of SEQ ID NO: 5 which includes the sequence GGP;

(28) a portion of SEQ ID NO: 5 which includes the sequence PE;

(29) a portion of SEQ ID NO: 5 which includes the sequence HS;

(30) a portion of SEQ ID NO: 5 which includes the sequence SV; and

(31) a portion of SEQ ID NO: 5 which includes the sequence FF.

Although the invention has been described with reference to embodiments and examples, it should be understood that various modifications can be made without departing from the spirit of the invention. Accordingly, the invention is limited only by the following claims.

REFERENCES

Each of the following references is incorporated herein by reference in its entirety:

1. Lawrence J F, Niedzwiadek B, Menard C. Quantitative determination of paralytic shellfish poisoning toxins in shellfish using prechromatographic oxidation and liquid chromatography with fluorescence detection: interlaboratory study. *J AOAC Int.* 2004, 87, 83-100.
2. Catterall, W. A., Ann. Rev. Biochem. 1986, 55, 953-985.
3. Shimizu, Y., Chem. Rev., 1993, 93, 1685-1698.
4. Taylor, F., in: *Toxic phytoplankton blooms in the sea*, (T. J. Smayda & Y. Shimizu eds), Elsevier Science Publishers, New York 1993, pp. 81-86.
5. Anderson, D. M., *Identification of harmful algal species using molecular probes*. Sixiéme Conference Internationale sur le Phytoplancton Toxique, Nantes, France, 18-22 Octobre 1993.
6. Vrieling, E. G. & Anderson, D. M., *J. Phycol.* 1996, 32: 1-16.
7. Jellett, J. F., Marks, L. J., Stewart J. E., Dorey, M. L., Watson-Wright W. et al., Toxicon, 1992, 30, 1143-1156.
8. AOAC (1990) Method 959-08, in Official Methods of Analyses, Association of Official Analytical Chemists, Arlington, Va. 15th Ed., pp. 881-882.
9. Sullivan, J. J., in: Marine Toxins: Origin, Structure, and Molecular Pharmacology (S. Hall and G. Strichartz eds.), Washington, American Chemical Society 1990, pp. 66-77.
10. Quilliam, M. A.; Janecek, M. and Lawrence, J. F., Rapid Commun. Mass Spect. 1993, 7, 482-487.
11. Maranda, L.; Anderson, D. M. and Shimizu, Y. Estuar. Coast. Shelf Sci. 1985, 21, 401-410.
12. Yentsch, C. M., Dale, B. and Hurst, J. W., J. Phycol. 1978, 14, 330-332.
13. Boyer, G. L; Sullivan, J. J. Anderson, R. J.; Harrison, P. J. and Taylor, F. J. R., Mar. Biol. 1987, 96, 23-128.
14. Oshima, Y; Blackburn, S. I. and Hallegraeff, G. M., Mar. Biol. 1993, 116(3), 471-476.
15. Anderson, D. M., Kulis, D. M.; Sullivan, J. J. and Hall, S., Toxicon 1990, 28. 885-893.
16. Wang, D & Hsieh, D. Toxicon 2001, 39:1533-1536.
17. Taroncher-Oldenburg, G., Kulis, D. M. and Anderson, D. M. Limnol. Oceanogr. 1997, 42, 1178-1188.
18. Shimizu, Y.; Gupta, S, and Prasad, A. V. K., in: Toxic Marine phytoplanlton. Proc. 4th Int. Conf. On Toxic Marine Phytoplankton (E. Graneli et al. eds), Elsevier, N.Y., Amsterdam and London 1990, pp. 271-274.
19. Oshima, Y., J. Assoc, Off. Anal, Chem. Intl., 1995, 78(2), March-April. P528-532.
20. Anderson, D. M. Sci. Am., August, 1994. pp. 52-58.
21. Palenik, B. & Wood, A. M. 1997. in: Molecular Approaches to the Study of the Oceans (Cooksley, K. E. ed.), Chapman and Hall, London 1997, pp. 187-205.
22. Chan, L. L., Hodgkiss, I. J. and Lo, S. C. L., Proteomics 2004, 4, 180-192.
23. Keller, M. D.; Selvin, R. C.; Claus, W.; Guillard, R. R. L., J. Phycol. 1987 23, 633-638.
24. Bechemin, C., Grzebyk, D., Hachame, F., Hummert, C., et al., Aquatic Microbial Ecology 1999, 20(2), 157-165.
25. Shevchenko, A. et al. Anal Chem 1996, 68, 850-858.
26. Balech E. The genus Alexandrium Halim (Dinoflagellata), Sherkin Island Marine Station, Sherkin Island, 1995, 151.
27. Wang C H et al. Biomed Environ Sci. 2003, 16(4):340-7.
28. Ogata, T.: Ishimaru, T. and Kodama, M., in: Red tides: Biology Environmental Science and Toxicology. Proc. 1st Int. Symp. on Red Tides (T. Okaichi et al. eds), Elsevier, N.Y. 1987, pp. 423-426.
29. Oshima Y., Hirota M., Yasumoto, T., Hallegraeff G. M., Blackburn, S. I., et al., Nippon Suisan Gakkaishi 1989, 55, 925.
30. Franco, J. M., Fernandez, P., Reguera, B., J. Appl. Phycol. 1994, 6, 275-279.
31. Anderson, D. M., Kulis, D. M., Sullivan, J. J., Hall, S, and Lee, C., Marine Biology 1990, 104, 511-524.
32. Loeblich, A. R. III., in: Dinoflagellates (D. L. Spector ed.), Academic Press, Orlando 1984, pp. 299-342.
33. Flynn, K., Jones, K. J., Flynn, K. J., Mar. Biol. 1996, 126, 9-18.
34. Doucette, G. J., Kodama, M., Franca, S. & Gallacher, S., in: Physiological ecology of harmful algal blooms. (D. M. Anderson, A. D. Cembella & G. M. Hallegraeff eds), Springer-Verlag, Berlin 1998, pp. 619-647.
35. Wilkins, M. R., William, K. L., J. Theor. Biol. 1997, 186, 7-15.

The invention claimed is:

1. A method for determining whether a naturally occurring strain of algae is toxic, comprising isolating a polypeptide from said strain of algae and determining whether a sample obtained from said strain of algae comprises an N-terminal peptide followed by a bio-marker sequence of amino acid residues, wherein said N-terminal peptide comprises the amino acid sequence SAEYL ERLGP KDADV PFTAA as set forth in SEQ ID NO: 1, and said bio-marker sequence is selected from the group consisting of GGA, TFK, GAE and KKR which indicates said strain of algae as being toxic.

2. The method according to claim 1, wherein said bio-marker sequence is 14 amino acid residues in length.

3. The method according to claim 2, wherein said bio-marker sequence comprises PGGAE HPVTF KKRP as set forth in residues 21-34 of SEQ ID NO:1 which indicates a toxic strain.

4. The method of claim 1, wherein the determining step is selected from the group consisting of 2-DE gel electrophoresis, ELISA assays, HPLC, peptide mass fingerprinting and MALDI-TOF mass spectrometry and fluorescence detection.

* * * * *

SEQUENCE LISTING

```
<160> NUMBER OF SEQ ID NOS: 10

<210> SEQ ID NO 1
<211> LENGTH: 158
<212> TYPE: PRT
<213> ORGANISM: Alexandrium Minutum

<400> SEQUENCE: 1

Ser Ala Glu Tyr Leu Glu Arg Leu Gly Pro Lys Asp Ala Asp Val Pro
 1               5                  10                  15
```

```
Phe Thr Ala Ala Pro Gly Gly Ala Glu His Pro Val Thr Phe Lys Lys
            20                  25                  30

Arg Pro Phe Gly Ile Leu Arg Tyr Gln Pro Gly Ala Gly Met Lys Gly
        35                  40                  45

Ala Met Val Met Glu Ile Ile Pro Lys Ser Arg Tyr Pro Gly Asp Pro
 50                  55                  60

Gln Gly Gln Ala Phe Ser Ser Gly Val Gln Ser Gly Trp Val Val Lys
 65                  70                  75                  80

Ser Ile Asn Gly Glu Asp Val Leu Thr Ala Asp Phe Gly Arg Ile Met
                85                  90                  95

Asp Leu Leu Asp Asp Glu Val Ala Asp Pro Arg Phe Ser Lys Ser Thr
            100                 105                 110

Ala Leu Ala Leu Glu Lys Gln Gly Gly Arg Leu Ala Ala Pro Val Glu
        115                 120                 125

Ala Pro Leu Gly Val Val Phe Ala Glu Ile Pro Gly Tyr Gln Gly Asn
    130                 135                 140

Phe Ala Thr Leu Ser Gln Asp Gly Gln Asp Gly Phe Ala Arg
145                 150                 155

<210> SEQ ID NO 2
<211> LENGTH: 476
<212> TYPE: DNA
<213> ORGANISM: Alexandrium Minutum

<400> SEQUENCE: 2
agtgccgagt acctagaacg actagggccc aaagacgcgg acgtgccctt cacggccgcc    60
cctggcggcg ctgagcaccc ggtgaccttc aagaagcggc ccttcggcat cttgcgctac   120
cagccgggcg cgggcatgaa gggtgccatg gtgatggaga tcattcccaa gtcgcgctac   180
cccggcgacc cccagggcca ggcgttctcc tcgggcgtgc agagcggatg ggtcgtcaag   240
tcgatcaacg gtgaggacgt gctgacggcg gacttcggcc gcatcatgga cttgctggac   300
gacgaggtgg ccgacccgcg cttctccaag tcgacggcct tggccctcga gaagcagggc   360
ggccgcttgg cagcgccggt ggaggcgccc ctcggggtcg tcttcgcgga gatcccgggc   420
taccagggca acttcgcgac gctcagccag gacggccagg acggcttcgc gcgtta       476

<210> SEQ ID NO 3
<211> LENGTH: 34
<212> TYPE: PRT
<213> ORGANISM: Alexandrium minutum

<400> SEQUENCE: 3

Ser Ala Glu Tyr Leu Glu Arg Leu Gly Pro Lys Asp Ala Asp Val Pro
 1               5                  10                  15

Phe Thr Ala Ala Ala Gly Gly Gly Glu Glu Pro Val Val Phe Asp Asp
            20                  25                  30

Arg Pro

<210> SEQ ID NO 4
<211> LENGTH: 34
<212> TYPE: PRT
<213> ORGANISM: Alexandrium minutum

<400> SEQUENCE: 4

Ser Ala Glu Tyr Leu Glu Arg Leu Gly Pro Lys Asp Ala Asp Val Pro
 1               5                  10                  15

Phe Thr Ala Ala Pro Gly Gly Pro Glu His Pro Val Thr Phe Asp Lys
            20                  25                  30
```

-continued

```
<210> SEQ ID NO 5
<211> LENGTH: 34
<212> TYPE: PRT
<213> ORGANISM: Alexandrium minutum

<400> SEQUENCE: 5

Ser Ala Glu Tyr Leu Glu Arg Leu Gly Pro Lys Asp Ala Asp Val Pro
1               5                   10                  15

Phe Thr Ala Ala Pro Gly Gly Pro Glu His Ser Val Thr Phe Phe Lys
            20                  25                  30

Arg Pro

<210> SEQ ID NO 6
<211> LENGTH: 31
<212> TYPE: PRT
<213> ORGANISM: Alexandrium Minutum

<400> SEQUENCE: 6

Ser Ala Glu Tyr Leu Glu Arg Leu Gly Pro Lys Asp Ala Asp Val Pro
1               5                   10                  15

Phe Thr Ala Ala Pro Gly Gly Ala Glu His Pro Val Thr Phe Lys
            20                  25                  30

<210> SEQ ID NO 7
<211> LENGTH: 37
<212> TYPE: DNA
<213> ORGANISM: Alexandrium Minutum
<220> FEATURE:
<223> OTHER INFORMATION: Primer

<400> SEQUENCE: 7
ggccacgcgt cgactagtac tttttttttt ttttttt                              37

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
cccaaagacg cggacgtgcc                                                 20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ggccacgcgt cgactagtac                                                 20

<210> SEQ ID NO 10
<211> LENGTH: 20
<212> TYPE: DNA
<213> ORGANISM: Artificial Sequence
```

```
<220> FEATURE:
<223> OTHER INFORMATION: Primer

<400> SEQUENCE: 10
gcggacgtgc ccttcacggc                                           20
```